United States Patent
Keller et al.

(10) Patent No.: US 11,111,541 B2
(45) Date of Patent: Sep. 7, 2021

(54) DIAGNOSTIC MIRNA MARKERS FOR PARKINSON'S DISEASE

(71) Applicant: Universitat des Saarlandes, Homberg (DE)

(72) Inventors: Andreas Keller, Puttlingen (DE); Cord Friedrich Stahler, Hirschberg an der Bergstrasse (DE); Jan Kirsten, Bamberg (DE); Eckart Meese, Huetschenhausen (DE); Christina Backes, Saarbrucken-Dudweiler (DE); Petra Leidinger, Wadern (DE)

(73) Assignee: Universitat Des Saarlandes, Homberg Saar (DE)

( * ) Notice: Subject to any disclaimer, the term of this patent is extended or adjusted under 35 U.S.C. 154(b) by 0 days.

(21) Appl. No.: 16/004,775

(22) Filed: Jun. 11, 2018

(65) Prior Publication Data
US 2018/0340228 A1    Nov. 29, 2018

Related U.S. Application Data

(63) Continuation of application No. 14/442,756, filed as application No. PCT/EP2013/065819 on Jul. 26, 2013, now Pat. No. 10,011,873.

(30) Foreign Application Priority Data

Nov. 16, 2012  (EP) .................................... 12192974
Nov. 16, 2012  (EP) .................................... 12192979

(51) Int. Cl.
*C12Q 1/6883*   (2018.01)
*G16B 25/00*   (2019.01)
*G16H 50/20*   (2018.01)

(52) U.S. Cl.
CPC .......... *C12Q 1/6883* (2013.01); *G16B 25/00* (2019.02); *G16H 50/20* (2018.01); *C12Q 2600/158* (2013.01); *C12Q 2600/178* (2013.01)

(58) Field of Classification Search
CPC ............ C12Q 1/6883; C12Q 2600/158; C12Q 2600/178
See application file for complete search history.

(56) References Cited

U.S. PATENT DOCUMENTS

| | | |
|---|---|---|
| 7,687,616 B1 | 3/2010 | Benywich et al. |
| 9,493,832 B2 | 11/2016 | Vilanova et al. |
| 2009/0081640 A1 | 3/2009 | Umansky et al. |
| 2010/0234445 A1 | 9/2010 | Lui et al. |
| 2010/0280099 A1 | 11/2010 | Elmen |
| 2012/0225925 A1 | 9/2012 | Sozzi et al. |
| 2015/0197805 A1 | 7/2015 | Umansky et al. |

FOREIGN PATENT DOCUMENTS

| | | |
|---|---|---|
| CN | 101861399 A | 10/2010 |
| EP | 2077326 A1 | 7/2009 |
| EP | 2112235 A1 | 10/2009 |
| WO | 2009/009457 A1 | 1/2009 |
| WO | 2009/025852 A2 | 2/2009 |
| WO | 2009/036236 A1 | 3/2009 |
| WO | 2011/057003 A2 | 5/2011 |
| WO | 2012/036433 A2 | 3/2012 |
| WO | 2012/145363 A1 | 10/2012 |
| WO | 2013/065819 A1 | 5/2013 |
| WO | 2013/072920 A2 | 5/2013 |
| WO | 2014/075911 A2 | 5/2014 |

OTHER PUBLICATIONS

Biomarkers Definitions Working Group, Arthur J. Atkinson Jr, Wayne A. Colburn, Victor G. DeGruttola, David L. DeMets, Gregory J. Downing, Daniel F. Hoth et al. "Biomarkers and surrogate endpoints: preferred definitions and conceptual framework." Clinical pharmacology & therapeutics 69, No. 3 (2001): 89-95.
De Smaele et al. "MicroRNAs as biomarkers for CNS cancer and other disorders." Brain research 1338 (2010): 100-111.
Friedländer, et al. "miRDeep2 accurately identifies known and hundreds of novel microRNA genes in seven animal clades." Nucleic acids research 40, No. 1 (2011): 37-52.
Geekiyanage, et al. "Blood serum miRNA: non-invasive biomarkers for Alzheimer's disease." Experimental neurology 235, No. 2 (2012): 491-496.
Keller, et al. "Toward the blood-borne miRNome of human diseases." Nature methods 8, No. 10 (2011): 841.
Kim, et al. "A MicroRNA feedback circuit in midbrain dopamine neurons." Science 317, No. 5842 (2007): 1220-1224.
Lange, et al. "miRNA Biomarkers From Blood-A Promising Approach for Minimally Invasive Diagnostic Testing." Geburtshilfe and Frauenheilkunde 70, No. 02 (2010): 137-141.
Maes, et al. "MicroRNA: implications for Alzheimer disease and other human CNS disorders." Current genomics 10, No. 3 (2009): 154-168.
Malaplate-Armand, et al. "Diagnostic biologique de la maladie d'Alzheimer: avancées, limites et perspectives." revue neurologique 165, No. 6-7 (2009): 511-520.
Margis, et al. "Identification of blood microRNAs associated to Parkinsońs disease." Journal of biotechnology 152, No. 3 (2011): 96-101.
Martins, et al. "Convergence of miRNA expression profiling, α-synuclein interacton and GWAS in Parkinson's disease." PloS one 6, No. 10 (2011): e25443.
Satoh "MicroRNAs and their therapeutic potential for human diseases: aberrant microRNA expression in Alzheimer's disease brains." Journal of pharmacological sciences 114, No. 3 (2010): 269-275.

(Continued)

*Primary Examiner* — Olga N Chernyshev
(74) *Attorney, Agent, or Firm* — Kilpatrick Townsend & Stockton LLP

(57) ABSTRACT

The invention relates to methods for diagnosing Parkinson's Disease PAD) with miRNA markers. Towards the identification of biomarkers for diagnosis of PD, a comprehensive analysis of miRNA expression patterns was obtained. Significantly deregulated miRNAs were identified.

14 Claims, 8 Drawing Sheets
Specification includes a Sequence Listing.

(56) References Cited

OTHER PUBLICATIONS

Schipper, et al. "MicroRNA expression in Alzheimer blood mononuclear cells." Gene regulation and systems biology 1 (2007): GRSB-S361.
Schulz, et al. "Characterization of three novel isoforms of the metabotrobic glutamate receptor 7 (GRM7)." Neuroscience letters 326, No. 1 (2002): 37-40.
Strimbu, et al. "What are biomarkers?." Current Opinion in HIV and AIDS 5, No. 6 (2010): 463.
Office Action dated Mar. 19, 2018 in U.S. Appl. No. 14/442,439.
Office Action dated Apr. 26, 2018 in U.S. Appl. No. 14/442,858.
Barbato, et al. "Searching for MIND: microRNAs in neurodegenerative diseases." BioMed Research International Aug. 23, 2009 (2009).
Gao et al., "Study on Parkinson's," Chinese Journal of Neurology, vol. 44, No. 11, Nov. 2011, 780-782.
Hudson, et al. "No consistent evidence for association between mtDNA variants and Alzheimer disease." Apr. 3, 2012; 78(14) Neurology (2012) 1038-42.

DIAGNOSTIC MIRNA MARKERS FOR PARKINSON'S DISEASE

PRIORITY STATEMENT

This application is a national phase application under 35 U.S.C. § 371 of PCT International Application No. PCT/EP2013/065819 which has an International filing date of 26 Jul. 2013, which designated the United States of American, and which claims priority to European patent application number 12192974.9 filed 16 Nov. 2012. The entire contents of each patent application referenced above are hereby incorporated by reference.

REFERENCE TO A SEQUENCE LISTING

This application contains references to amino acid sequences and/or nucleic acid sequences 15 which have been submitted concurrently herewith as the sequence listing text file 61494540_1.TXT file size 33.9 KiloBytes (KB), created on 5 Aug. 2013. The aforementioned sequence listing is hereby incorporated by reference in its entirety pursuant to 37 C.F.R. § 1.52 (e)(5).

FIELD OF THE INVENTION

The invention relates to novel markers for Parkinson's disease (PD).

BACKGROUND OF THE INVENTION

Very recently, molecular diagnostics has increasingly gained in importance. It has found an entry into the clinical diagnosis of diseases (inter alia detection of infectious pathogens, detection of mutations of the genome, detection of diseased cells and identification of risk factors for predisposition to a disease).

In particular, through the determination of gene expression in tissues, nucleic acid analysis opens up very promising new possibilities in the study and diagnosis of disease.

Nucleic acids of interest to be detected include genomic DNA, expressed mRNA and other RNAs such as MicroRNAs (abbreviated miRNAs). MiRNAs are a new class of small RNAs with various biological functions (A. Keller et al., Nat Methods. 2011 8(10):841-3). They are short (average of 20-24 nucleotide) ribonucleic acid (RNA) molecules found in eukaryotic cells. Several hundred different species of microRNAs (i.e. several hundred different sequences) have been identified in mammals. They are important for posttranscriptional gene-regulation and bind to complementary sequences on target messenger RNA transcripts (mRNAs), which can lead to translational repression or target degradation and gene silencing. As such they can also be used as biologic markers for research, diagnosis and therapy purposes.

Parkinson's disease (P) is a degenerative disorder of the central nervous system. The motor symptoms of Parkinson's disease result from the death of dopamine-generating cells in the nervous system; the cause of this cell death is unknown.

Early symptoms are often mistaken to be age-related problems. Parkinson's disease affects movement, producing motor symptoms and may cause mood, cognition, behavior or thought alterations. Diagnosis of Parkinson's disease is based on the medical history and a neurological examination. There is no lab test that will clearly identify the disease, but imaging modalities are sometimes used to rule out other disorders. Symptoms, such as frailty and motor symptoms can be similar to other neurological disorders. Diagnosis can be time consuming, expensive and difficult. In particular, the reliable and early diagnosis of Parkinson based on non-invasive molecular biomarkers remains a challenge.

Therefore, there exists an unmet need for an efficient, simple, reliable diagnostic test for PD.

OBJECT OF THE INVENTION

The technical problem underlying the present invention is to provide biological markers allowing to diagnose, screen for or monitor Parkinson's disease, predict the risk of developing Parkinson's disease, or predict an outcome of Parkinson's disease.

SUMMARY OF THE INVENTION

Before the invention is described in detail, it is to be understood that this invention is not limited to the particular component parts of the process steps of the methods described as such methods may vary. It is also to be understood that the terminology used herein is for purposes of describing particular embodiments only, and is not intended to be limiting. It must be noted that, as used in the specification and the appended claims, the singular forms "a," "an" and "the" include singular and/or plural referents unless the context clearly dictates otherwise. It is also to be understood that plural forms include singular and/or plural referents unless the context clearly dictates otherwise. It is moreover to be understood that, in case parameter ranges are given which are delimited by numeric values, the ranges are deemed to include these limitation values.

In its most general terms, the invention relates to a collection of miRNA markers useful for the diagnosis, prognosis and prediction of Parkinson's Disease.

DETAILED DESCRIPTION OF THE INVENTION

Definitions

Figure 1:
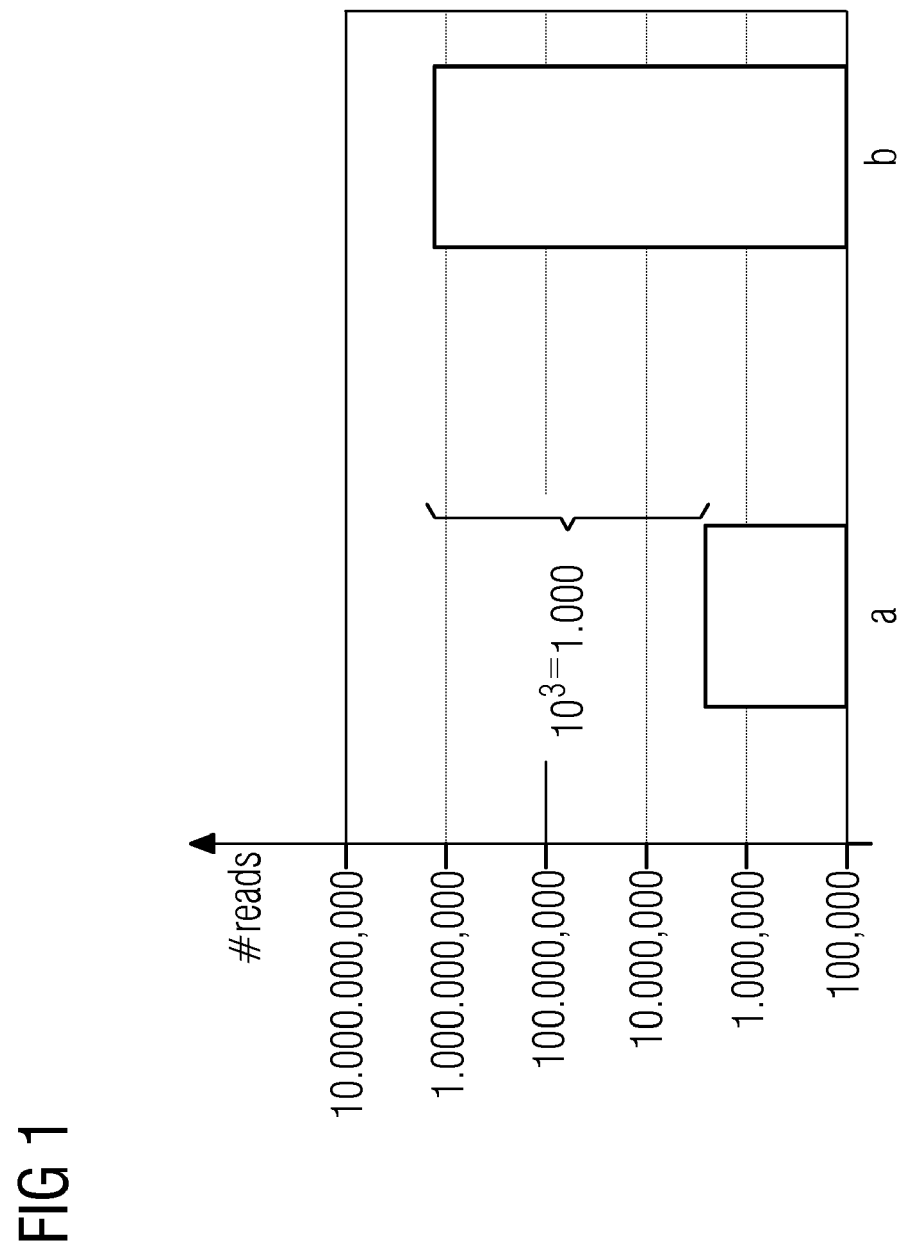
FIG. 1 shows the distribution of novel nucleic acid molecule miRNA markers (a) of the invention vs. known miRNA markers (b) in blood.

Unless defined otherwise, technical and scientific terms used herein have the same meaning as commonly understood by one of ordinary skill in the art to which this invention belongs.

The term "predicting an outcome" of a disease, as used herein, is meant to include both a prediction of an outcome of a patient undergoing a given therapy and a prognosis of a patient who is not treated.

An "outcome" within the meaning of the present invention is a defined condition attained in the course of the disease. This disease outcome may e.g. be a clinical condition such as "relapse of disease", "remission of disease", "response to therapy", a disease stage or grade or the like.

A "risk" is understood to be a probability of a subject or a patient to develop or arrive at a certain disease outcome. The term "risk" in the context of the present invention is not meant to carry any positive or negative connotation with regard to a patient's wellbeing but merely refers to a probability or likelihood of an occurrence or development of a given event or condition.

The term "clinical data" relates to the entirety of available data and information concerning the health status of a patient including, but not limited to, age, sex, weight, menopausal/hormonal status, etiopathology data, anamnesis data, data obtained by in vitro diagnostic methods such as blood or urine tests, data obtained by imaging methods, such as x-ray, computed tomography, MRI, PET, spect, ultrasound, electrophysiological data, genetic analysis, gene expression analysis, biopsy evaluation, intraoperative findings.

The term "classification of a sample" of a patient, as used herein, relates to the association of said sample with at least one of at least two categories. These categories may be for example "high risk" and "low risk"; or high, intermediate and low risk; wherein risk is the probability of a certain event occurring in a certain time period, e.g. occurrence of disease, progression of disease, etc. It can further mean a category of favourable or unfavourable clinical outcome of disease, responsiveness or non-responsiveness to a given treatment or the like. Classification may be performed by use of an algorithm, in particular a discrimant function. A simple example of an algorithm is classification according to a first quantitative parameter, e.g. expression level of a nucleic acid of interest, being above or below a certain threshold value. Classification of a sample of a patient may be used to predict an outcome of disease or the risk of developing a disease. Instead of using the expression level of a single nucleic acid of interest, a combined score of several nucleic acids of interest of interest may be used. Further, additional data may be used in combination with the first quantitative parameter. Such additional data may be clinical data from the patient, such as sex, age, weight of the patient, disease grading etc.

A "discriminant function" is a function of a set of variables used to classify an object or event. A discriminant function thus allows classification of a patient, sample or event into a category or a plurality of categories according to data or parameters available from said patient, sample or event. Such classification is a standard instrument of statistical analysis well known to the skilled person. E.g. a patient may be classified as "high risk" or "low risk", "in need of treatment" or "not in need of treatment" or other categories according to data obtained from said patient, sample or event. Classification is not limited to "high vs. low", but may be performed into a plurality of categories, grading or the like. Examples for discriminant functions which allow a classification include, but are not limited to discriminant functions defined by support vector machines (SVM), k-nearest neighbors (kNN), (naive) Bayes models, or piecewise defined functions such as, for example, in subgroup discovery, in decision trees, in logical analysis of data (LAD) an the like.

The term "expression level" refers, e.g., to a determined level of expression of a nucleic acid of interest. The term "pattern of expression levels" refers to a determined level of expression com-pared either to a reference nucleic acid, e.g. from a control, or to a computed average expression value, e.g. in DNA-chip analyses. A pattern is not limited to the comparison of two genes but is also related to multiple comparisons of genes to reference genes or samples. A certain "pattern of expression levels" may also result and be determined by comparison and measurement of several nucleic acids of interest disclosed hereafter and display the relative abundance of these transcripts to each other. Expression levels may also be assessed relative to expression in different tissues, patients versus healthy controls, etc.

A "reference pattern of expression levels", within the meaning of the invention shall be understood as being any pattern of expression levels that can be used for the comparison to another pattern of expression levels. In a preferred embodiment of the invention, a reference pattern of expression levels is, e.g., an average pattern of expression levels observed in a group of healthy or diseased individuals, serving as a reference group.

In the context of the present invention a "sample" or a "biological sample" is a sample which is derived from or has been in contact with a biological organism. Examples for biological samples are: cells, tissue, body fluids, biopsy specimens, blood, urine, saliva, sputum, plasma, serum, cell culture supernatant, and others.

A "probe" is a molecule or substance capable of specifically binding or interacting with a specific biological molecule. The term "primer", "primer pair" or "probe", shall have ordinary meaning of these terms which is known to the person skilled in the art of molecular biology. In a preferred embodiment of the invention "primer", "primer pair" and "probes" refer to oligonucleotide or polynucleotide molecules with a sequence identical to, complementary too, homologues of, or homologous to regions of the target molecule or target sequence which is to be detected or quantified, such that the primer, primer pair or probe can specifically bind to the target molecule, e.g. target nucleic acid, RNA, DNA, cDNA, gene, transcript, peptide, polypeptide, or protein to be detected or quantified. As understood herein, a primer may in itself function as a probe. A "probe" as understood herein may also comprise e.g. a combination of primer pair and internal labeled probe, as is common in many commercially available qPCR methods.

A "gene" is a set of segments of nucleic acid that contains the information necessary to produce a functional RNA product in a controlled manner. A "gene product" is a biological molecule produced through transcription or expression of a gene, e.g. an mRNA or the translated protein.

A "miRNA" is a short, naturally occurring RNA molecule and shall have the ordinary meaning understood by a person skilled in the art. A "molecule derived from a miRNA" is a molecule which is chemically or enzymatically obtained from an miRNA template, such as cDNA.

The term "array" refers to an arrangement of addressable locations on a device, e.g. a chip device. The number of locations can range from several to at least hundreds or thousands.

Each location represents an independent reaction site. Arrays include, but are not limited to nucleic acid arrays, protein arrays and antibody-arrays. A "nucleic acid array" refers to an array containing nucleic acid probes, such as oligonucleotides, polynucleotides or larger portions of genes. The nucleic acid on the array is preferably single stranded. A "microarray" refers to a biochip or biological chip, i.e. an array of regions having a density of discrete regions with immobilized probes of at least about 100/cm2.

A "PCR-based method" refers to methods comprising a polymerase chain reaction PCR. This is a method of exponentially amplifying nucleic acids, e.g. DNA or RNA by enzymatic replication in vitro using one, two or more primers. For RNA amplification, a reverse transcription may be used as a first step. PCR-based methods comprise kinetic or quantitative PCR (qPCR) which is particularly suited for the analysis of expression levels,). When it comes to the determination of expression levels, a PCR based method may for example be used to detect the presence of a given mRNA by (1) reverse transcription of the complete mRNA pool (the so called transcriptome) into cDNA with help of a reverse transcriptase enzyme, and (2) detecting the presence of a given cDNA with help of respective primers. This approach is commonly known as reverse transcriptase PCR (rtPCR). The term "PCR based method" comprises both end-point PCR applications as well as kinetic/real time PCR techniques applying special fluorophors or intercalating dyes which emit fluorescent signals as a function of amplified target and allow monitoring and quantification of the target. Quantification methods could be either absolute by external standard curves or relative to a comparative internal standard.

The term "next generation sequencing" or "high throughput sequencing" refers to high-throughput sequencing technologies that parallelize the sequencing process, producing thousands or millions of sequences at once. Examples include Massively Parallel Signature Sequencing (MPSS) Polony sequencing, 454 pyrosequencing, Illumina (Solexa) sequencing, SOLiD sequencing, Ion semiconductor sequencing, DNA nanoball sequencing, Helioscope™ single molecule sequencing, Single Molecule SMRT™ sequencing, Single Molecule real time (RNAP) sequencing, Nanopore DNA sequencing.

The term "marker" or "biomarker" refers to a biological molecule, e.g., a nucleic acid, peptide, protein, hormone, etc., whose presence or concentration can be detected and correlated with a known condition, such as a disease state, or with a clinical outcome, such as response to a treatment.

In particular, the invention relates to a method of classifying a sample of a patient suffering from or at risk of developing Parkinson's Disease, wherein said sample is a blood sample, said method comprising the steps of:

a) determining in said sample an expression level of at least one miRNA selected from the group consisting of miRNAs having the sequence SEQ ID NO 69, SEQ ID NO 142, SEQ ID NO 2, SEQ ID NO 59, SEQ ID NO 58 and SEQ ID NO 65;

b) comparing the pattern of expression level(s) determined in step a) with one or several reference pattern(s) of expression levels; and c) classifying the sample of said patient from the outcome of the comparison in step b) into one of at least two classes.

These sequences correspond to the following miRNAs: miR-1285-5p (SEQ ID NO: 69), miR-151-3p (SEQ ID NO: 58), hsa-let-7f (SEQ ID NO: 2) and miR-5010 (SEQ ID NO: 65) and newly discovered miRNAs, namely brain-mir-112 (SEQ ID NO: 59) and brain-mir-161 (SEQ ID NO: 142), A reference pattern of expression levels may, for example, be obtained by determining in at least one healthy subject the expression level of at least one miRNA selected from the group consisting of miRNAs having the sequence SEQ ID NO 69, SEQ ID NO 142, SEQ ID NO 2, SEQ ID NO 59, SEQ ID NO 58 and SEQ ID NO 65.

A reference pattern of expression levels may, for example, further be obtained by determining in at least one patient having another neurological disease the expression level of at least one miRNA selected from the group consisting of miRNAs having the sequence SEQ ID NO 69, SEQ ID NO 142, SEQ ID NO 2, SEQ ID NO 59, SEQ ID NO 58 and SEQ ID NO 65. Examples for other neurological disease include Alzheimer's Disease (AD) Cognitive Impairment (MCI), Multiple Sclerosis (herein also referred to as Clinically Isolated Syndrome, CIS), Mild Depression (n=15), Bipolar Disorder (BD), and Schizophrenia (Schiz).

It is within the scope of the invention to assign a numerical value to an expression level of the at least one miRNA determined in step a).

It is further within the scope of the invention to mathematically combine expression level values to obtain a pattern of expression levels in step (b), e.g. by applying an algorithm to obtain a normalized expression level relative to a reference pattern of expression level(s).

In a further aspect the invention relates to a method for diagnosing Parkinson's Disease, predicting risk of developing Parkinson's Disease, or predicting an outcome of Parkinson's Disease in a patient suffering from or at risk of developing Parkinson's Disease, said method comprising the steps of:

a) determining in a blood sample from said patient, the expression level of at least one miRNA selected from the group consisting of miRNAs with the sequence SEQ ID NO 69, SEQ ID NO 142, SEQ ID NO 2, SEQ ID NO 59, SEQ ID NO 58 and SEQ ID NO 65;

b) comparing the pattern of expression level(s) determined in step a) with one or several reference pattern(s) of expression levels; and c) diagnosing Parkinson's Disease, predicting a risk of developing Parkinson's Disease, or predicting an outcome of Parkinson's Disease from the outcome of the comparison in step b).

According to an aspect of the invention, said at least one miRNA is selected from the group consisting of miRNAs with the sequence SEQ ID NO 69, SEQ ID NO 142, SEQ ID NO 2, SEQ ID NO 59, SEQ ID NO 58 and SEQ ID NO 65.

According to an aspect of the invention, the expression levels of a plurality of miRNAs are determined as expression level values and step (b) comprises mathematically combining the expression level values of said plurality of miRNAs.

It is within the scope of the invention to apply an algorithm to the numerical value of the expression level of the at least one miRNA determined in step a) to obtain a disease score to allow classification of the sample or diagnosis, prognosis or prediction of the risk of developing Parkinson's Disease, or prediction of an outcome of Parkinson's Disease. A non-limiting example of such an algorithm is to compare the numerical value of the expression level against a threshold value in order to classify the result into one of two categories, such as high risk/low risk, diseased/healthy or the like. A further non-limiting example of such an algorithm is to combine a plurality of numerical values of expression levels, e.g. by summation, to obtain a combined score. Individual summands may be normalized or weighted by multiplication with factors or numerical values representing the expression level of a miRNA, numerical values representing clinical data, or other factors.

It is within the scope of the invention to apply a discriminant function to classify a result, diagnose disease, predict an outcome or a risk.

According to an aspect of the invention, the expression level in step (a) is obtained by use of a method selected from the group consisting of a sequencing-based method, an array based method and a PCR based method.

According to an aspect of the invention, the expression levels of at least 2, 3, 4, 5, or 6, miRNAs are determined to obtain a pattern of expression levels.

The invention further relates to a kit for performing the methods of the invention, said kit comprising
means for determining in said blood sample from said patient, an expression level of at least one miRNA selected from the group consisting of miRNAs with the sequence SEQ ID NO 69, SEQ ID NO 142, SEQ ID NO 2, SEQ ID NO 59, SEQ ID NO 58 and SEQ ID NO 65.

The means for determining the expression level of said at least one miRNA may comprise an oligonucleotide probe for detecting or amplifying said at least one miRNA, means for determining the expression level based on an array-based method, a PCR based method, a sequencing based method or any other suitable means for determining the expression level.

According to an aspect of the invention, the kit further comprises at least one reference pattern of expression levels for comparing with the expression level of the at least one miRNA from said sample. The reference pattern of expression may include at least one digital or numerical information and may be provided in any readable or electronically readable form, including, but not limited to printed form, electronically stored form on a computer readable medium, such as CD, smart card, or provided in downloadable form, e.g. in a computer network such as the internet.

The invention further relates to computer program product useful for performing the methods of the invention, comprising
means for receiving data representing an expression level of at least one miRNA in a patient blood sample selected from the group consisting of miRNAs with the sequence SEQ ID NO 69, SEQ ID NO 142, SEQ ID NO 2, SEQ ID NO 59, SEQ ID NO 58 and SEQ ID NO 65,
means for receiving data representing at least one reference pattern of expression levels for comparing with the expression level of the at least one miRNA from said sample,
means for comparing said data representing the expression level of the at least one miRNA in a patient sample, and
optionally means for determining a diagnosis of Parkinson's Disease, a prediction of a risk of developing Parkinson's Disease, or a prediction of an outcome of Parkinson's Disease from the outcome of the comparison in step b).

The computer program product may be provided on a storable electronic medium, such as a solid state memory, disk, CD or other. It may be stored locally on a computer. It may be implemented as network-based program or application, including a web- or internet-based application. It may be implemented in a diagnostic device, such as an analyzer instrument.

It may be operably connected to a device for outputting information, such as a display, printer or the like.

EXAMPLES

Additional details, features, characteristics and advantages of the object of the invention are further disclosed in the following description and figures of the respective examples, which, in an exemplary fashion, show preferred embodiments of the present invention. However, these examples should by no means be understood as to limit the scope of the invention.

The invention relates to methods for diagnosing Parkinson's Disease with miRNA markers.

Diagnosis of Parkinson's Disease can be challenging in patients presenting with generally age-related syndromes such as frailty. In particular, it is difficult to diagnose the earliest stages of disease. However, it would be particularly desirable to have a reliable diagnostic test for this stage of disease, as the chance of therapeutic and social intervention is improved during this early disease stage.

Here, the abundance of miRNAs in blood samples of Parkinson's Disease patients has been compared in an unbiased approach against healthy controls and patients suffering from other neuronal disorders. This approach involved a massive effort of sequencing miRNAs from samples and thus was open to the discovery of novel markers not yet described in the prior art. Further, the use of blood samples as a source of expression information of miRNA markers has several tangible advances which are not available in other sample sources such as serum or tissue, such as ease of sample procurement and handling, sample preparation, and robustness and consistency of expression patterns.

Materials and Methods

Patient Cohorts

The expression of miRNAs in peripheral blood of a total of 219 patients and healthy controls was determined, either by NGS or by qRT-PCR or both. Blood was obtained from patients with Parkinson's Disease (PD) (n=9), patients with Alzheimer's Disease (AD) (n=106), patients with Mild Cognitive Impairment (MCI) (n=21), patients with Multiple Sclerosis (Clinically Isolated Syndrome, CIS) (n=17), patients with Mild Depression (DEP) (n=15), Bipolar Disorder (BD) (n=15), Schizophrenia (Schiz) (n=14), and from healthy controls (n=22).

First, samples from AD patients (n=48), MCI patients (n=20) and healthy controls (n=22) were analyzed by Next-generation sequencing. For validation purposes the expression of single miRNAs was analyzed using qRT-PCR in the same samples as used for NGS, if enough RNA was available. The number of samples was further expanded by further samples from patients with AD, CIS, PD, DEP, BD, and Schiz, resulting in a total of 205 samples analyzed by qRT-PCR. In detail, a total of 95 samples from AD patients, 19 samples from MCI patients, 17 samples from CIS patients, 9 samples from PD patients, 15 samples from DEP patients, 15 samples from BD patients, 14 samples from Schiz patients, and 21 samples from healthy controls were analyzed.

RNA Isolation

Total RNA including miRNA was isolated using the PAXgene Blood miRNA Kit (Qiagen) following the manufacturer's recommendations. Isolated RNA was stored at −80° C. RNA integrity was analyzed using Bioanalyzer 2100 (Agilent) and concentration and purity were measured using NanoDrop 2000 (Thermo Scientific). A total of four samples (three controls and one RRMS) failed the quality criteria and were excluded from the study.

Library Preparation and Next-Generation Sequencing

For the library preparation, 200 ng of total RNA was used per sample, as determined with a RNA 6000 Nano Chip on the Bioanalyzer 2100 (Agilent). Preparation was performed following the protocol of the TruSeq Small RNA Sample Prep Kit (Illumina). Concentration of the ready prepped libraries was measured on the Bioanalyzer using the DNA 1000 Chip. Libraries were then pooled in batches of six samples in equal amounts and clustered with a concentration of 9 pmol in one lane each of a single read flowcell using the cBot (Illumina). Sequencing of 50 cycles was performed on a HiSeq 2000 (Illumina). Demultiplexing of the raw sequencing data and generation of the fastq files was done using CASAVA v.1.8.2.

NGS Data Analysis

The raw illumina reads were first preprocessed by cutting the 3' adapter sequence using the programm fastx_clipper from the FASTX-Toolkit (Website: hannonlab.cshl/fastx_toolkit). Reads shorter than 18 nts after clipping were removed. The remaining reads are reduced to unique reads and their frequency per sample to make the mapping steps more time efficient. For the remaining steps, we used the miRDeep2 pipeline. These steps consist of mapping the reads against the genome (hg19), mapping the reads against miRNA precursor sequences from mirbase release v18, summarizing the counts for the samples, and the prediction of novel miRNAs. Since the miRDeep2 pipeline predicts novel miRNAs per sample, the miRNAs were merged afterwards as follows: first, the novel miRNAs per sample that have a signal-to-noise ratio of more than 10 were extracted. Subsequently, only those novel miRNAs that are located on the same chromosome were merged, and both their mature forms share an overlap of at least 11 nucleotides.

In particular, six miRNA markers were selected for their ability to differentiate between PD and (healthy) controls as well as PD and other neurological diseases. Out of the NGS results these six miRNAs were selected, since they were deregulated in both the comparison between patients with Parkinson's Disease and patients with other neurological disease, and the comparison between patients with Parkinson's Disease and healthy individuals. Four of the six miRNAs, namely miR-1285-5p (SEQ ID NO: 69), miR-151-3p (SEQ ID NO: 58), hsa-let-7f (SEQ ID NO: 2) and miR-5010 (SEQ ID NO: 65) were already known mature miRNAs included in miRBase, two miRNAs, namely brain-mir-112 (SEQ ID NO: 59) and brain-mir-161 (SEQ ID NO: 142), were newly identified and not yet included in miR-Base.

The miScript PCR System (Qiagen) was used for reverse transcription and qRT-PCR. A total of 200 ng RNA was converted into cDNA using the miScript Reverse Transcription Kit according to the manufacturers' protocol. For each RNA we additionally prepared 5 µl reactions containing 200 ng RNA and 4 µl of the 5× miScript RT Buffer but no miScript Reverse Transcriptase Mix, as negative control for the reverse transcription (RT-control). The qRT-PCR was performed with the miScript SYBR® Green PCR Kit in a total volume of 20 µl per reaction containing 1 µl cDNA according to the manufacturers' protocol. For each miScript Primer Assay we additionally prepared a PCR negative-control with water instead of cDNA (non-template control, NTC).

Bioinformatics Analysis

First the read counts were normalized using standard quantile normalization. All miRNAs with less than 50 read counts were excluded from further considerations. Next, we calculated for each miRNA the area under the receiver operator characteristic curve (AUC), the fold-change, and the significance value (p-value) using t-tests. All significance values were adjusted for multiple testing using the Benjamini Hochberg approach. The bioinformatics analyses have been carried out using the freely available tool. Furthermore, we carried out a miRNA enrichment analysis using the TAM tool (Website: 202.38.126.151/hmdd/tools/tam.html).

Computing Combined Scores

Briefly, to compute a combined expression score for n up-regulated markers and m downregulated markers the difference d between the expression value $x_{(a)}$ of a patient a and the average expression value of all controls µ is determined. For down-regulated markers, the difference can be multiplied by (−1), thus yielding a positive value. The differences for n markers can be added up to yield a combined score Z, such that $$Z_{(a)} = \Sigma d_{(1-n)}(\text{upregulated}) + \Sigma(-1)d_{(1-m)}(\text{down-regulated})$$

Wherein $$d = x_{(a)} - \mu$$

To make combined scores between different marker scores comparable (e.g. to compare a (n+m)=7 marker score against a (n+m)=12 marker score, the combined score can be divided by (n+m):

$$Z\text{comp} = 1/(n+m)(\Sigma d_{(1-n)}(\text{upregulated}) + \Sigma(-1)d_{(1-m)}(\text{down-regulated}))$$

Other factors can be applied to the individual summands d of the combined score or the combined score Z as a whole.

Results

The most abundant miRNAs were hsa-miR-486-5p with an average read-count of 13,886,676 and a total of 1.2 billion reads mapping to this miRNA, hsa-miR-92a-3p with an average of 575,359 reads and a total of 52 million reads mapping to this miRNA and miR-451a with an average of 135,012 reads and a total of 12 million reads mapping to this miRNA.

The invention provides very rare variants of miRNAs that are present in blood cells. While common variants have already been discovered and are heavily overlapping with miRNAs discovered from tissue biopsies, a substantial part of miRNAs is expected to be still unknown. Herein, patients suffering neurological disorders including mild cognitive impairment, Alzheimers disease or multiple sclerosis as well as unaffected controls were characterized.

About 2 billion sequences from the patient and control samples were generated, of which around 1.4 billion matched to known or predicted novel miRNAs. As detailed in FIG. 1, the vast majority of these sequences matched known miRNAs (99.9%) while only around 0.1% matched to predicted novel miRNAs, pointing out why the enormous sequencing capacity had to be used. It has been found that these novel miRNAs can be used as diagnostic markers indicative of disease conditions such as neuronal diseases, e.g. Parkinsons's Disease.

These miRNA candidates have generally however been much less abundant as compared to the known human miRNAs.

Figure 2:
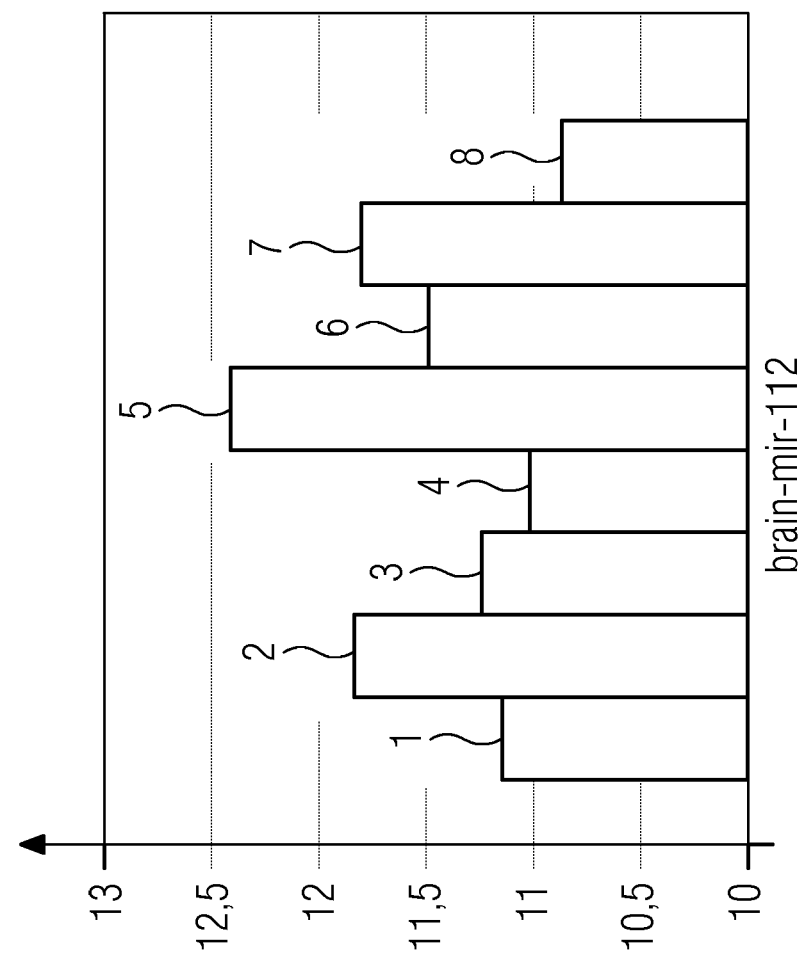
FIG. 2 shows delta CT values of a first exemplary novel nucleic acid molecule miRNA marker of the invention, brain-mir-112, in samples of patients having different neuronal disorders and controls.
Figure 3:
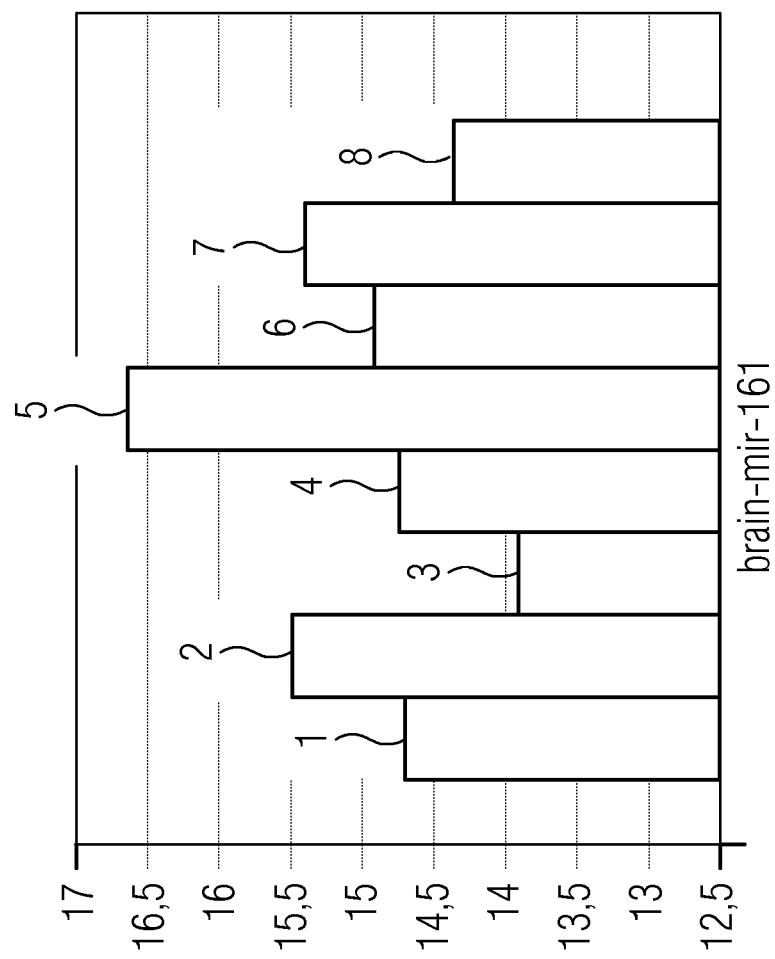
FIG. 3 shows delta CT values of a further exemplary novel nucleic acid molecule miRNA marker of the invention, brain-mir-161 in different samples of patients having different neuronal disorders and controls.
Figure 4:
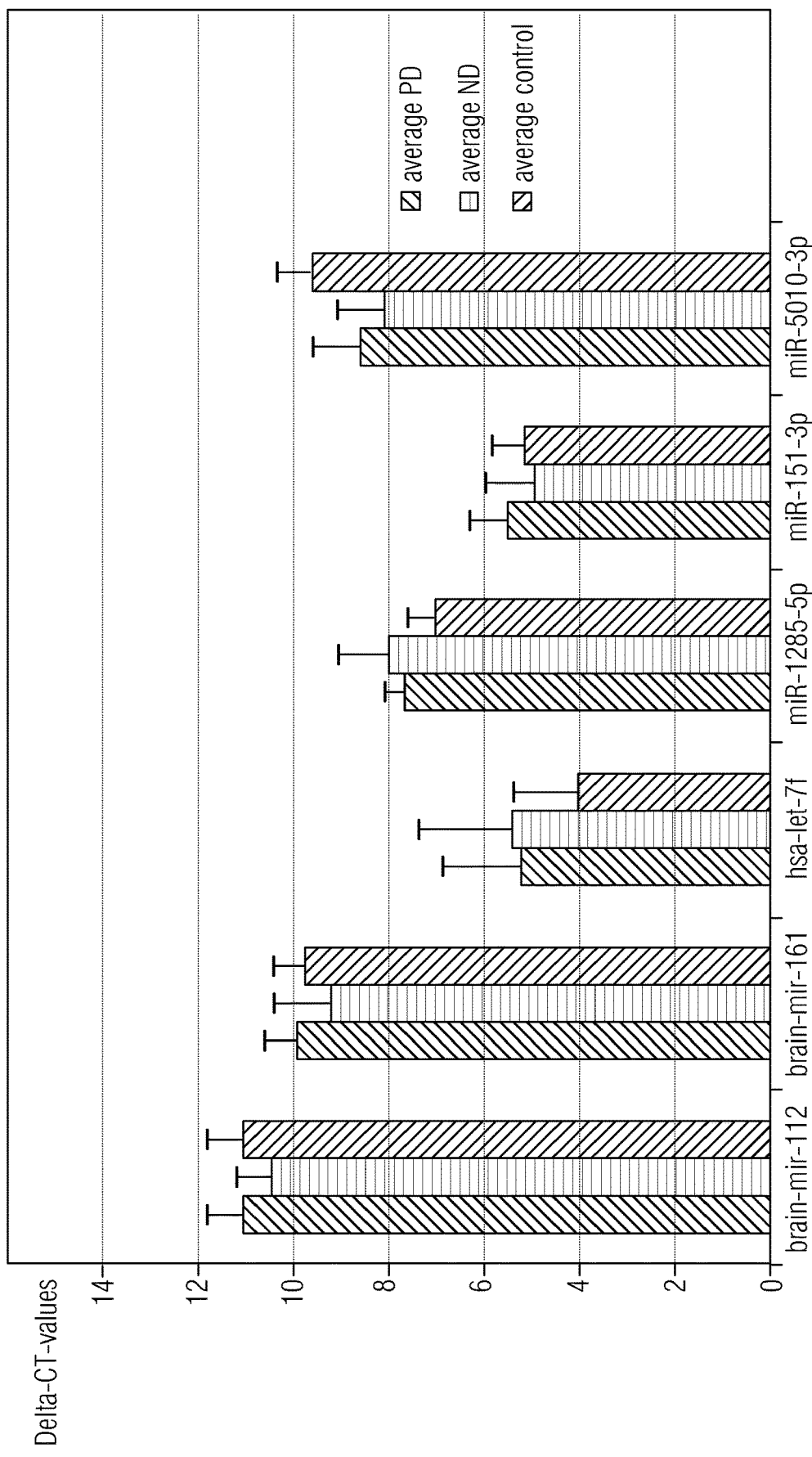
FIG. 4 shows delta CT values of six miRNA markers in different samples of patients having Parkinsons's disease, different neuronal disorders (ND) and healthy controls.
Figure 5:
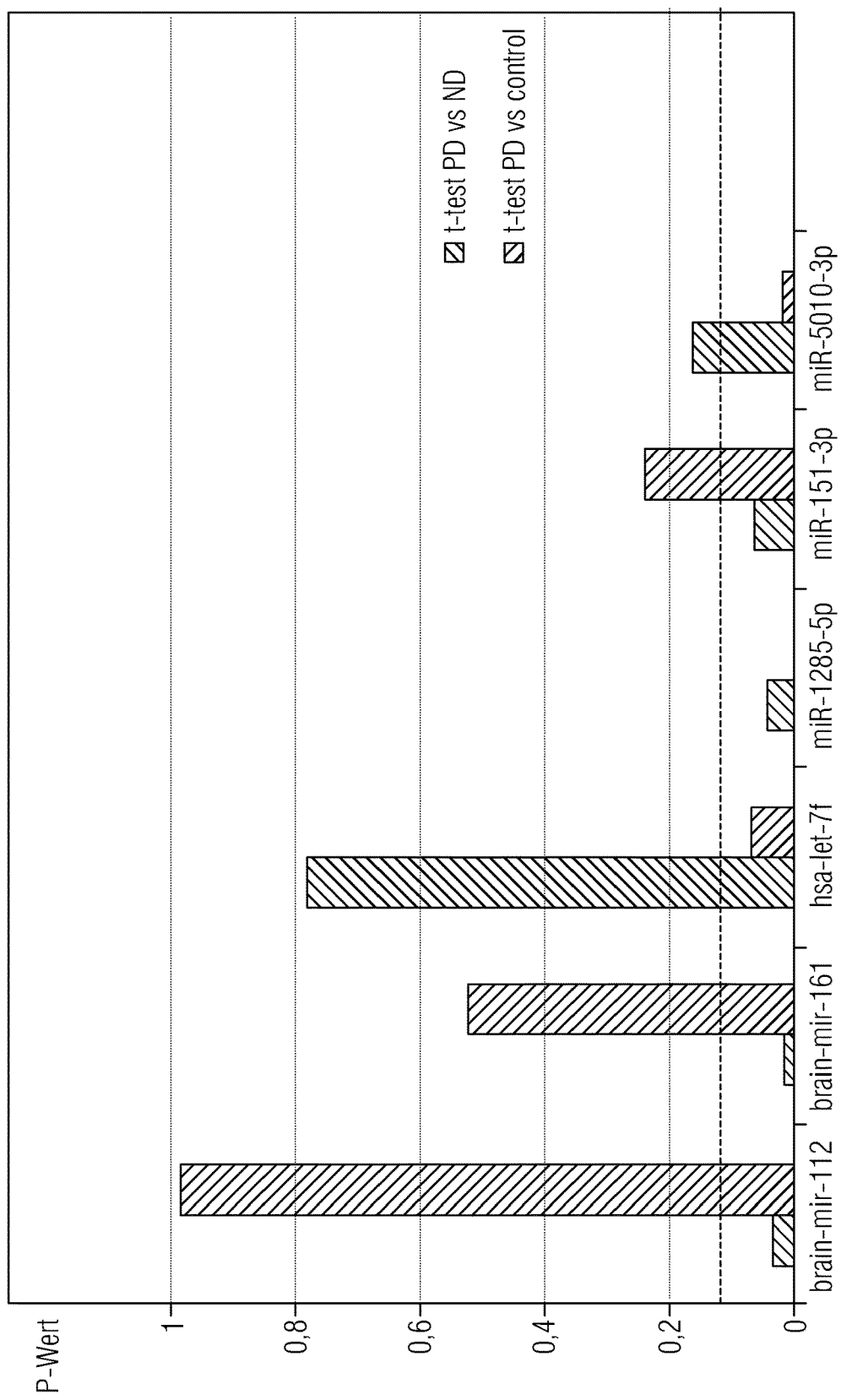
FIG. 5 shows t-test values of of six miRNA markers in different samples of patients having Parkinsons's disease vs different neuronal disorders (ND) and healthy controls.

In FIG. 2 and FIG. 3 the delta CT values of a first exemplary novel nucleic acid molecule miRNA marker of the invention, brain-mir-112, and of a further exemplary novel nucleic acid molecule miRNA marker of the invention, brain-mir-161, in samples of patients having different Neurological diseases AD (two cohorts), BD, CIS, DEP, MCI, and Schiz (col. 1, 3-8) and controls (col. 2).

A list of all miRNA molecules described herein is given in Supplemental Table 2 containing an overview of the miRNA markers, including sequence information.

It is noted that the mature miRNa originate from miRNA precursor molecules of length of around 120 bases. Several examples exists where the miRNA precursors vary from each other while the subset of the around 20 bases belonging to the mature miRNA are identical. Thus, novel mature miRNAs can have the same sequence but different SEQ ID NO identifiers.

MiRNA markers are denoted by their common name (e.g. has-miR-144-5p or hsa-let 7f-5p) and are searchable in publically available databases. In this invention there are also described novel miRNA markers which have been named with names beginning with the prefix "brain-miR". They are listed in supplemental table 1 with their sequence and their SEQ ID NO according to the sequence protocol.

Besides single markers, combinations of multiple markers have demonstrated a potential to improve the diagnostic accuracy. We selected a signature of just 6 markers, known markers Four of the six miRNAs, namely miR-1285-5p (SEQ ID NO: 69), miR-151-3p (SEQ ID NO: 58), hsa-let-7f (SEQ ID NO: 2) and miR-5010 (SEQ ID NO: 65) and new markers brain-mir-112 (SEQ ID NO: 59) and brain-mir-161 (SEQ ID NO: 142). To combine the values of the 6 miRNAs in one score can be calculated the average z-score as detailed in the Material & Methods section. A combination of the six markers gives an improved differentiation between PD vs. controls and between PD vs. other neurological diseases.

Scores of Other Neurological Disorders

Figure 6:
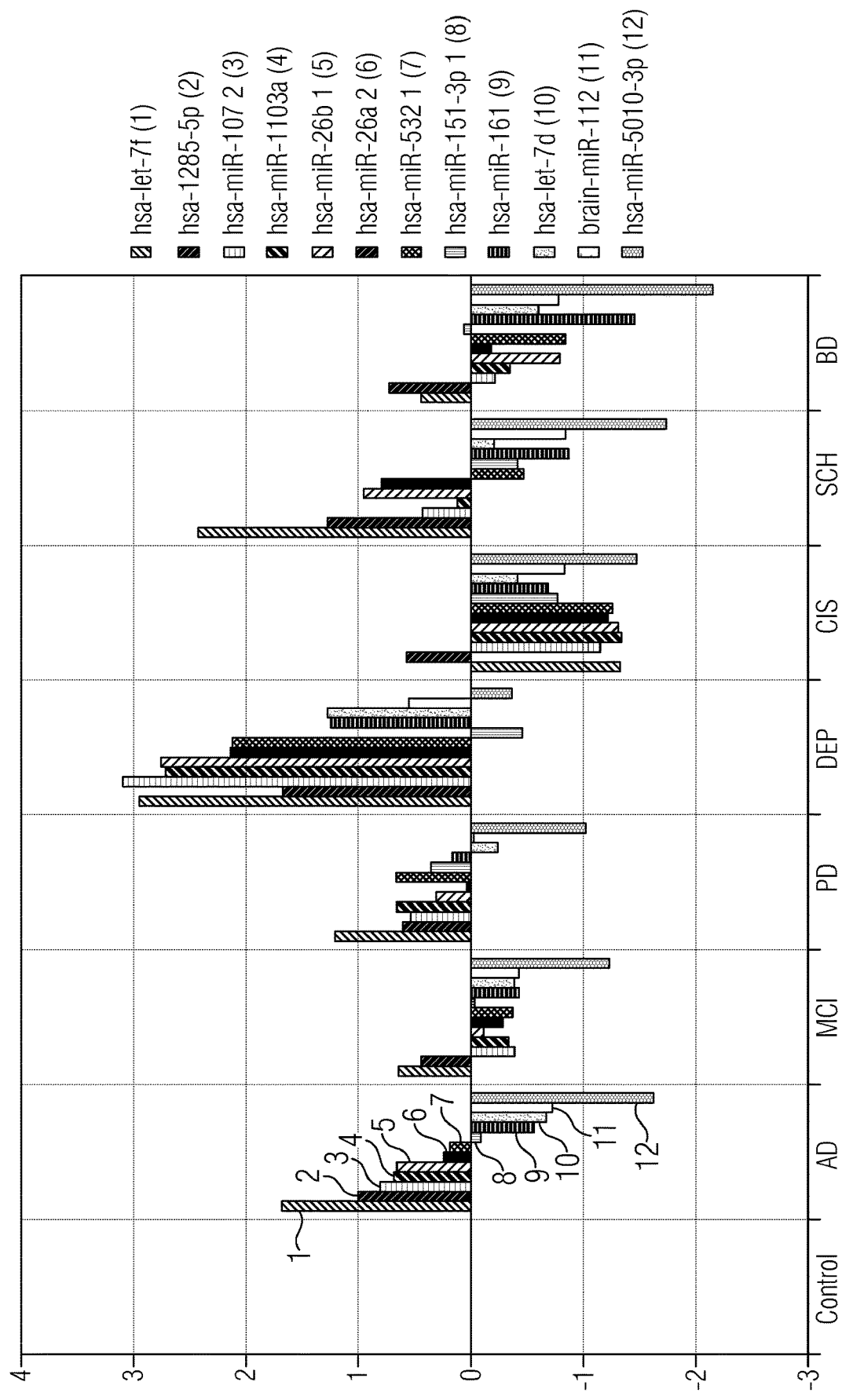
FIG. 6 shows the validation of 12 miRNAs in 7 diseases (AD, MCI, PD, DEP, CIS, SCH, and BD and controls). The 12 miRNAs are (denoted by columns 1-12, respectively) hsa-let-7f-5p, hsa-miR-1285-5p, hsa-miR-107, hsa-miR-103a-3p, hsa-miR-26b-3p, hsa-miR-26a-5p, hsa-miR-532-5p, hsa-miR-151a-3p, brain-mir-161, hsa-let-7d-3p, brain-mir-112, and hsa-miR-5010-3p.
Figure 7:
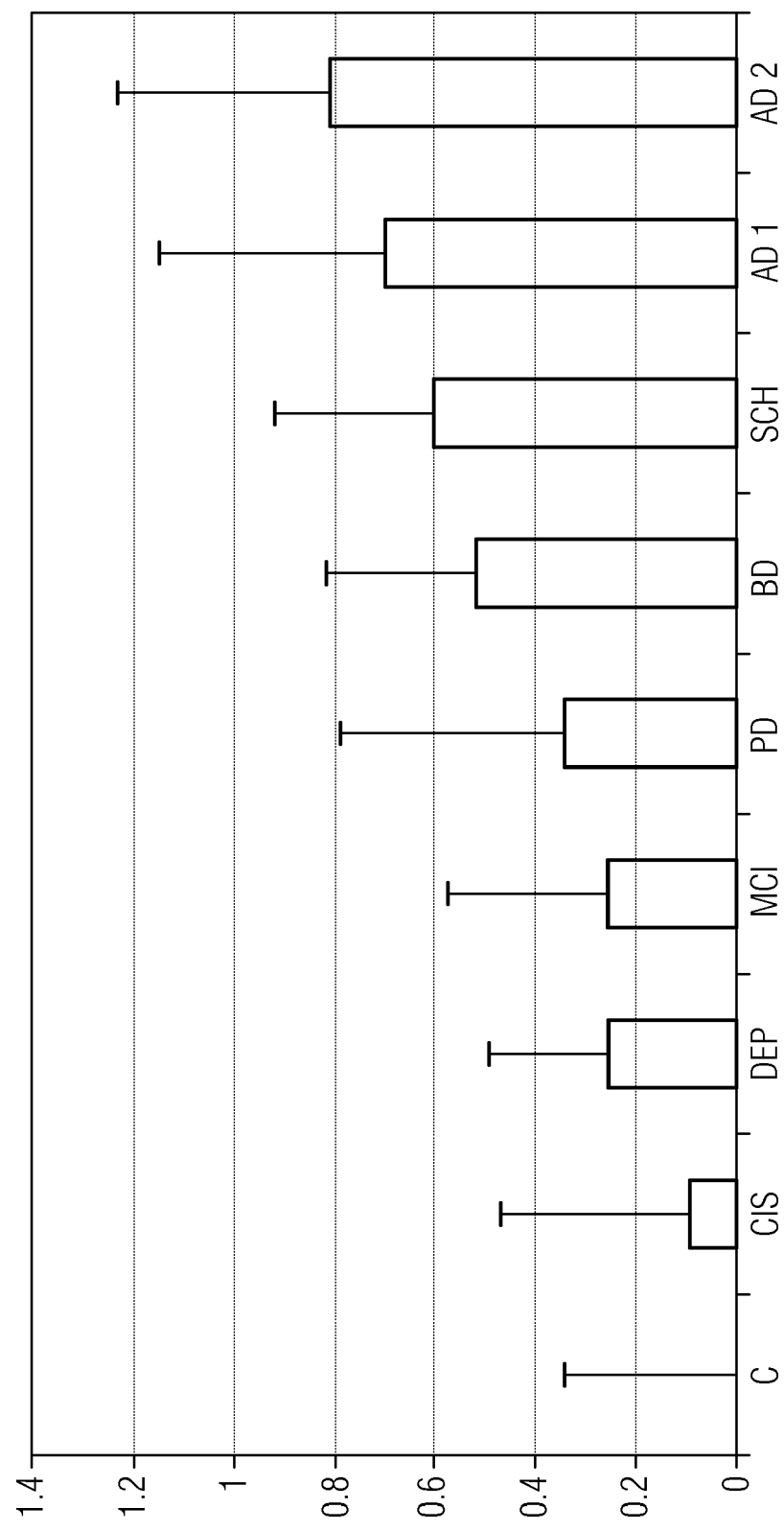
FIG. 7 shows the combined score of the 7-miRNA signature brain-mir-112, hsa-miR-5010-3p, hsa-miR-103a-3p, hsa-miR-107, hsa-let-7d-3p, hsa-miR-532-5p, and brainmir-161 for all diseases. The combined score (y-axis) was obtained using quantitative RT PCR.
Figure 8:
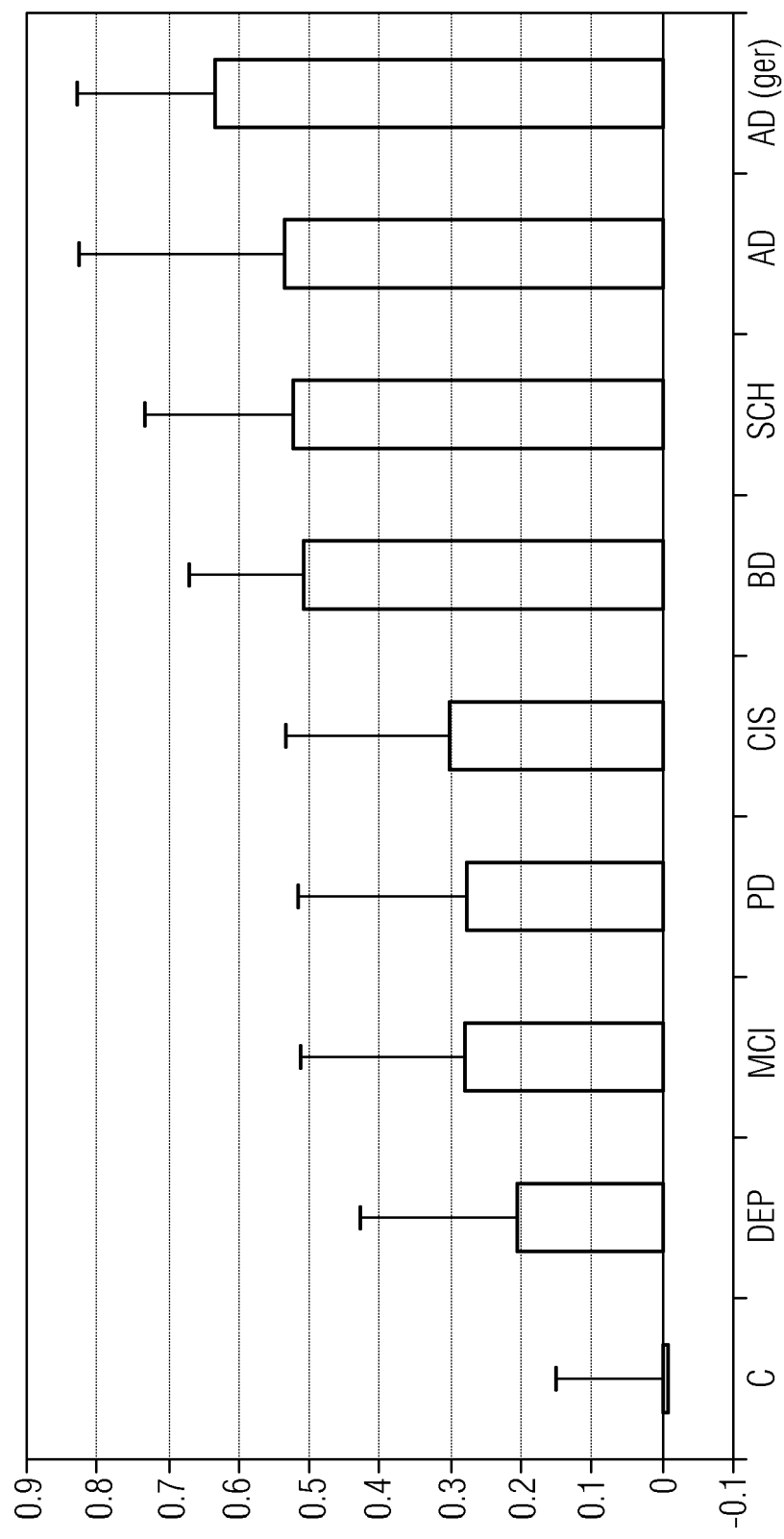
FIG. 8 shows the combined score of the 12-miRNA signature hsa-let-7f-5p, hsa-miR-1285-5p, hsa-miR-107, hsa-miR-103a-3p, hsa-miR-26b-3p, hsa-miR-26a-5p, hsa-miR-532-5p, hsa-miR-151a-3p, brain-mir-161, hsa-let-7d-3p, brain-mir-112, and hsa-miR-5010-3p for all diseases. The combined score (y-axis) was obtained using quantitative RT PCR.

Next the question was asked whether a cohort of other neurological disorders shows likewise significant deviations to controls. We measured samples of patients with Parkinson disease, Alzheimer's disease, mild cognitive impairment, schizophrenia, bipolar disorder, multiple sclerosis (CIS) and depression patients for a signature of 7 miRNAs, namely hsa-miR-5010-3p, hsa-miR-103a-3p, hsa-miR-107, hsa-let-7d-3p, hsa-miR-532-5p, brain-mir-112 and brain-mir-161. In FIG. 6, the bar diagrams for all diseases and all miRNAs are present. Here, the Alzheimer patients score is set to 0, as described earlier we have four down- and three up-regulated miRNAs for the controls. For mild cognitive impairment patients the same four miRNAs were down- and the same three miRNAs were upregulated, providing strong evidence that the MCI signature is much closer to controls as compared to AD. For CIS patients only two miRNAs were down-regulated, while the third one was not dysregulated and the remaining three were strongly up-regulated. For Parkinson disease, the first 5 miRNAs were down—while the remaining two were strongly upregulated. For Schizophrenia and Bipolar Disease, almost all miRNAs were strongly upregulated, in contrast, for Depression all miRNAs were significantly down-regulated. In summary, the results promise that AD can not only be distinguished from controls but also very well from other neurological disorders. Of course the same z-score based approach can be applied as for the Alzheimer and control patients in order to get an overall score for each cohort.

In Tables 1 and 2, an evaluation of expression values for miR-1285-5p (SEQ ID NO: 69), miR-151-3p (SEQ ID NO: 58), hsa-let-7f (SEQ ID NO: 2), miR-5010 (SEQ ID NO: 65), brain-mir-112 (SEQ ID NO: 59), and brain-mir-161 (SEQ ID NO: 142) in PD patients, combined other neurological disease patients and healthy controls are shown.

TABLE 1

Evaluation of Expression Values for brain-mir-112 brain-mir-161 hsa-let-7f

|  | brain-mir-112 | brain-mir-161 | hsa-let-7f |
|---|---|---|---|
| average PD | 11.03491038 | 9.898887474 | 5.25843664 |
| average ND | 10.42592681 | 9.227711302 | 5.419797676 |
| average control | 11.03017957 | 9.726909301 | 4.050352325 |
| sd PD | 0.702870335 | 0.668545504 | 1.633235375 |
| sd ND | 0.740377036 | 1.153414403 | 1.965260211 |
| sd control | 0.61149943 | 0.653667163 | 1.345809868 |
| t-test PD vs ND | 0.032518756 | 0.017686328 | 0.781348899 |
| t-test PD vs control | 0.9862585 | 0.52560265 | 0.072863496 |

TABLE 2

Evaluation of Expression Values for miR-1285-5p miR-151-3p miR-5010-3p

|  | miR-1285-5p | miR-151-3p | miR-5010-3p |
|---|---|---|---|
| average PD | 7.652496732 | 5.52538961 | 8.591982107 |
| average ND | 7.999877681 | 4.975099637 | 8.093307165 |
| average control | 7.034357049 | 5.15991191 | 9.599724944 |
| sd PD | 0.401429288 | 0.776236856 | 0.961903123 |
| sd ND | 1.019311517 | 1.000358415 | 0.961563715 |
| sd control | 0.561150883 | 0.672757054 | 0.720844163 |
| t-test PD vs ND | 0.041164926 | 0.070290871 | 0.164327666 |
| t-test PD vs control | 0.002636065 | 0.240353234 | 0.015373015 |

The focused analysis of miRNAs in large cohorts and the comparison with other neurological diseases allows to improve the specificity of miRNA markers or marker combinations. This enables an identification of PD patients by in-vitro diagnostics Tracking changes in the expression pattern of markers allows to monitor progression of disease and response to therapy.

The miRNAs described herein are also potential targets for highly specific therapy of Parkinson patients.

Supplemental Table 1,
Newly discovered miRNA markers

| SEQ ID NO | miRNA | Sequence |
|---|---|---|
| 126 | brain-mir-102 | UAUGGAGGUCUCUGUCUGGCU |
| 111 | brain-mir-111 | CACUGCUAAAUUUGGCUGGCUU |
| 59 | brain-mir-112 | AGCUCUGUCUGUGUCUCUAGG |

Supplemental Table 1, Newly discovered miRNA markers

| SEQ ID NO | miRNA | Sequence |
|---|---|---|
| 91 | brain-mir-114 | CACUGCAACCUCUGCCUCCGGU |
| 97 | brain-mir-12 | ACUCCCACUGCUUGACUUGACUAG |
| 160 | brain-mir-129 | CAUGGUCCAUUUUGCUCUGGU |
| 54 | brain-mir-145 | AAGCACUGCCUUUGAACCUGA |
| 23 | brain-mir-149 | AAAAGUAAUCGCACUUUUUG |
| 41 | brain-mir-150 | UGAGGUAGUAGGUGGUGUGC |
| 24 | brain-mir-151 | AAAAGUAAUCGCACUUUUUG |
| 121 | brain-mir-153 | CCUCUUCUCAGAACACUUCCUGG |
| 157 | brain-mir-160 | CACUGCAACCUCUGCCUCC |
| 142 | brain-mir-161 | CUUCGAAAGCGGCUUCGGCU |
| 116 | brain-mir-166 | CUGGCUGCUUCCCUUGGUCU |
| 21 | brain-mir-170 | AAAAGUAAUGGCAGUUUUUG |
| 138 | brain-mir-188 | CCUGACCCCAUGUCGCCUCUGU |
| 139 | brain-mir-189 | CCUGACCCCAUGUCGCCUCUGU |
| 137 | brain-mir-190 | CCUGACCCCAUGUCGCCUCUGU |
| 140 | brain-mir-192 | CCUGACCCCAUGUCGCCUCUGU |
| 117 | brain-mir-193 | AUCCCUUUAUCUGUCCUCUAGG |
| 88 | brain-mir-200 | UUCCUGGCUCUCUGUUGCACA |
| 107 | brain-mir-201 | CACCCCACCAGUGCAGGCUG |
| 100 | brain-mir-219 | UCAAGUGUCAUCUGUCCCUAGG |
| 124 | brain-mir-220 | UCCGGAUCCGGCUCCGCGCCU |
| 146 | brain-mir-23 | UUAGUGGCUCCCUCUGCCUGCA |
| 98 | brain-mir-232 | UUGCUCUGCUCUCCCUUGUACU |
| 94 | brain-mir-247 | ACGCCCACUGCUUCACUUGAGUAG |
| 50 | brain-mir-248S | GGCGGCGGAGGCGGCGGUG |
| 113 | brain-mir-251 | UGGCCCAAGACCUCAGACC |
| 169 | brain-mir-258 | AUCCCACCCCUGCCCCCA |
| 110 | brain-mir-279 | AUCCCACCGCUGCCACAC |
| 156 | brain-mir-293 | UUGGUGAGGACCCCAAGCUCGG |
| 120 | brain-mir-299 | CAUGCCACUGCACUCCAGCCU |
| 68 | brain-mir-308 | CACUGCACUCCAGCCUGGGUGA |
| 141 | brain-mir-311 | CACUGCAACCUCUGCCUCCCGA |
| 96 | brain-mir-314 | ACUCCCACUGCUUCACUUGAUUAG |
| 150 | brain-mir-319 | CUGCACUCCAGCCUGGGCGA |
| 27 | brain-mir-333 | AAAAGUAAUCGCAGGUUUUG |
| 148 | brain-mir-351 | UGUCUUGCUCUGUUGCCCAGGU |
| 25 | brain-mir-370 | GGCUGGUCUGAUGGUAGUGGGUUA |
| 84 | brain-mir-390 | ACUGCAACCUCCACCUCCUGGGU |
| 125 | brain-mir-392 | CCCGCCUGUCUCUCUCUUGCA |
| 19 | brain-mir-394 | AAAAGUAAUCGUAGUUUUUG |
| 67 | brain-mir-395 | CACUGCACUCCAGCCUGGGUGA |
| 38 | brain-mir-398 | GGCUGGUCCGAGUGGAGUGGUGUU |
| 134 | brain-mir-399 | CACUGCAACCUCUGCCUCC |
| 135 | brain-mir-403 | AAAGACUUCCUUCUCUCGCCU |
| 106 | brain-mir-41S | CCCCGCGCAGGUUCGAAUCCUG |
| 99 | brain-mir-424S | CACUGCACUCCAGCCUGGGUA |
| 73 | brain-mir-431 | CUCGGCCUUUGCUCGCAGCACU |
| 103 | brain-mir-52 | CUGCACUCCAGCCUGGGCGAC |
| 104 | brain-mir-53 | CCCAGGAGAGUUUCAGUGAUG |
| 131 | brain-mir-72S | GACCACACUCCAUCCUGGGC |
| 136 | brain-mir-73 | UCCGGAUGUGCUGACCCCUGCG |
| 80 | brain-mir-79 | CACUGCACUCCAGCCUGGCU |
| 81 | brain-mir-80 | CACUGCACUCCAGCCUGGCU |
| 76 | brain-mir-83 | CAGGGUCUCGUUCUGUUGCC |
| 112 | brain-mir-88 | UCUUCACCUGCCUCUGCCUGCA |

Supplemental Table 2
Overview of miRNA markers, including sequence information

| | | |
|---|---|---|
| 1 | hsa-miR-144-5p | GGAUAUCAUCAUAUACUGUAAG |
| 2 | hsa-let-7f-5p | UGAGGUAGUAGAUUGUAUAGUU |
| 3 | hsa-let-7e-5p | UGAGGUAGGAGGUUGUAUAGUU |
| 4 | hsa-let-7a-5p | UGAGGUAGUAGGUUGUAUAGUU |
| 5 | hsa-miR-107 | AGCAGCAUUGUACAGGGCUAUCA |
| 6 | hsa-let-7g-5p | UGAGGUAGUAGUUUGUACAGUU |
| 7 | hsa-miR-103a-3p | AGCAGCAUUGUACAGGGCUAUGA |
| 8 | hsa-miR-98 | UGAGGUAGUAAGUUGUAUUGUU |
| 9 | hsa-miR-29c-3p | UAGCACCAUUUGAAAUCGGUUA |
| 10 | hsa-miR-101-3p | UACAGUACUGUGAUAACUGAA |
| 11 | hsa-miR-548h-5p | AAAAGUAAUCGCGGUUUUUGUC |
| 12 | hsa-miR-106b-3p | CCGCACUGUGGGUACUUGCUGC |
| 13 | hsa-miR-15a-5p | UAGCAGCACAUAAUGGUUUGUG |
| 14 | hsa-miR-548g-5p | UGCAAAAGUAAUUGCAGUUUUUG |

Supplemental Table 2
Overview of miRNA markers, including sequence information

| | | |
|---|---|---|
| 15 | hsa-miR-548ar-5p | AAAAGUAAUUGCAGUUUUUGC |
| 16 | hsa-miR-548x-5p | UGCAAAAGUAAUUGCAGUUUUG |
| 17 | hsa-miR-548aj-5p | UGCAAAAGUAAUUGCAGUUUUUG |
| 18 | hsa-let-7c | UGAGGUAGUAGGUUGUAUGGUU |
| 19 | brain-mir-394 | AAAAGUAAUCGUAGUUUUUG |
| 20 | hsa-miR-1294 | UGUGAGGUUGGCAUUGUUGUCU |
| 21 | brain-mir-170 | AAAAGUAAUGGCAGUUUUUG |
| 22 | hsa-miR-199a-3p | ACAGUAGUCUGCACAUUGGUUA |
| 23 | brain-mir-149 | AAAAGUAAUCGCACUUUUUG |
| 24 | brain-mir-151 | AAAAGUAAUCGCACUUUUUG |
| 25 | brain-mir-370 | GGCUGGUCUGAUGGUAGUGGGUUA |
| 26 | hsa-miR-199b-3p | ACAGUAGUCUGCACAUUGGUUA |
| 27 | brain-mir-333 | AAAAGUAAUCGCAGGUUUUUG |
| 28 | hsa-miR-628-3p | UCUAGUAAGAGUGGCAGUCGA |
| 29 | hsa-miR-190a | UGAUAUGUUUGAUAUAUUAGGU |
| 30 | hsa-miR-29b-3p | UAGCACCAUUUGAAAUCAGUGUU |
| 31 | hsa-miR-660-5p | UACCCAUUGCAUAUCGGAGUUG |
| 32 | hsa-miR-143-3p | UGAGAUGAAGCACUGUAGCUC |
| 33 | hsa-miR-548av-5p | AAAAGUACUUGCGGAUUU |
| 34 | hsa-miR-548k | AAAAGUACUUGCGGAUUUUGCU |
| 35 | hsa-miR-29a-3p | UAGCACCAUCUGAAAUCGGUUA |
| 36 | hsa-miR-548i | AAAAGUAAUUGCGGAUUUUGCC |
| 37 | hsa-miR-17-3p | ACUGCAGUGAAGGCACUUGUAG |
| 38 | brain-mir-398 | GGCUGGUCCGAGUGCAGUGGUGUU |
| 39 | hsa-miR-148a-3p | UCAGUGCACUACAGAACUUUGU |
| 40 | hsa-miR-126-3p | UCGUACCGUGAGUAAUAAUGCG |
| 41 | brain-mir-150 | UGAGGUAGUAGGUGGUGUGC |
| 42 | hsa-let-7i-5p | UGAGGUAGUAGUUUGUGCUGUU |
| 43 | hsa-miR-33b-5p | GUGCAUUGCUGUUGCAUUGC |
| 44 | hsa-miR-3200-3p | CACCUUGCGCUACUCAGGUCUG |
| 45 | hsa-miR-548o-5p | AAAAGUAAUUGCGGUUUUUGCC |
| 46 | hsa-miR-152 | UCAGUGCAUGACAGAACUUGG |
| 47 | hsa-miR-548am-5p | AAAAGUAAUUGCGGUUUUUGCC |
| 48 | hsa-miR-548au-5p | AAAAGUAAUUGCGGUUUUUGC |
| 49 | hsa-miR-548c-5p | AAAAGUAAUUGCGGUUUUUGCC |
| 50 | brain-mir-248S | GGCGGCGGAGGCGGCGGUG |
| 51 | hsa-miR-215 | AUGACCUAUGAAUUGACAGAC |
| 52 | hsa-miR-340-5p | UUAUAAAGCAAUGAGACUGAUU |
| 53 | hsa-miR-1301 | UUGCAGCUGCCUGGGAGUGACUU |
| 54 | brain-mir-145 | AAGCACUGCCUUUGAACCUGA |
| 55 | hsa-miR-504 | AGACCCUGGUCUGCACUCUAUC |
| 56 | hsa-miR-30d-5p | UGUAAACAUCCCCGACUGGAAG |
| 57 | hsa-miR-4781-3p | AAUGUUGGAAUCCUCGCUAGAG |
| 58 | hsa-miR-151a-3p | CUAGACUGAAGCUCCUUGAGG |
| 59 | brain-mir-112 | AGCUCUGUCUGUGUCUCUAGG |
| 60 | hsa-miR-28-3p | CACUAGAUUGUGAGCUCCUGGA |
| 61 | hsa-miR-26b-3p | CCUGUUCUCCAUUACUUGGCUC |
| 62 | hsa-miR-1468 | CUCCGUUUGCCUGUUUCGCUG |
| 63 | hsa-miR-128 | UCACAGUGAACCGGUCUCUUU |
| 64 | hsa-miR-550a-5p | AGUGCCUGAGGGAGUAAGAGCCC |
| 65 | hsa-miR-5010-3p | UUUUGUGUCUCCCAUUCCCAG |
| 66 | hsa-miR-148b-5p | AAGUUCUGUUAUACACUCAGGC |
| 67 | brain-mir-395 | CACUGCACUCCAGCCUGGGUGA |
| 68 | brain-mir-308 | CACUGCACUCCAGCCUGGGUGA |
| 69 | hsa-miR-1285-5p | GAUCUCACUUUGUUGCCCAGG |
| 70 | hsa-miR-5001-3p | UUCUGCCUCUGUCCAGGUCCUU |
| 71 | hsa-miR-3127-3p | UCCCUUCUGCAGGCCUGCUGG |
| 72 | hsa-miR-3157-3p | CUGCCCUAGUCUAGCUGAAGCU |
| 73 | brain-mir-431 | CUCGGCCUUUGCUCGCAGCACU |
| 74 | hsa-miR-550a-3-5p | AGUGCCUGAGGGAGUAAGAG |
| 75 | hsa-miR-361-5p | UUAUCAGAAUCUCCAGGGGUAC |
| 76 | brain-mir-83 | CAGGGUCUCGUUCUGUUGCC |
| 77 | hsa-miR-589-5p | UGAGAACCACGUCUGCUCUGAG |
| 78 | hsa-miR-425-5p | AAUGACACGAUCACUCCCGUUGA |
| 79 | hsa-miR-30a-5p | UGUAAACAUCCUCGACUGGAAG |
| 80 | brain-mir-79 | CACUGCACUCCAGCCUGGCU |
| 81 | brain-mir-80 | CACUGCACUCCAGCCUGGCU |
| 82 | hsa-miR-330-5p | UCUCUGGGCCUGUGUCUUAGGC |
| 83 | hsa-miR-186-5p | CAAAGAAUUCUCCUUUUGGGCU |
| 84 | brain-mir-390 | ACUGCAACCUCCACCUCCUGGGU |
| 85 | hsa-let-7d-3p | CUAUACGACCUGCUGCCUUUCU |
| 86 | hsa-miR-328 | CUGGCCCUCUCUGCCCUUCCGU |

Supplemental Table 2
Overview of miRNA markers, including sequence information

| | | |
|---|---|---|
| 87 | hsa-miR-30c-5p | UGUAAACAUCCUACACUCUCAGC |
| 88 | brain-mir-200 | UUCCUGGCUCUCUGUUGCACA |
| 89 | hsa-miR-363-3p | AAUUGCACGGUAUCCAUCUGUA |
| 90 | hsa-miR-339-3p | UGAGCGCCUCGACGACAGAGCCG |
| 91 | brain-mir-114 | CACUGCAACCUCUGCCUCCGGU |
| 92 | hsa-miR-942 | UCUUCUCUGUUUGGCCAUGUG |
| 93 | hsa-miR-345-5p | GCUGACUCCUAGUCCAGGGCUC |
| 94 | brain-mir-247 | ACGCCCACUGCUUCACUUGACUAG |
| 95 | hsa-miR-4742-3p | UCUGUAUUCUCCUUUGCCUGCAG |
| 96 | brain-mir-314 | ACUCCCACUGCUUCACUUGAUUAG |
| 97 | brain-mir-12 | ACUCCCACUGCUUGACUUGACUAG |
| 98 | brain-mir-232 | UUGCUCGCUCUCCCUUGUACU |
| 99 | brain-mir-424S | CACUGCACUCCAGCCUGGGUA |
| 100 | brain-mir-219 | UCAAGUGUCAUCUGUCCCUAGG |
| 101 | hsa-miR-10a-5p | UACCCUGUAGAUCCGAAUUUGUG |
| 102 | hsa-miR-3605-3p | CCUCCGUGUUACCUGUCCUCUAG |
| 103 | brain-mir-52 | CUGCACUCCAGCCUGGGCGAC |
| 104 | brain-mir-53 | CCCAGGACAGUUUCAGUGAUG |
| 105 | hsa-miR-3157-5p | UUCAGCCAGGCUAGUGCAGUCU |
| 106 | brain-mir-41S | CCCCGCGCAGGUUCGAAUCCUG |
| 107 | brain-mir-201 | CACCCCACCAGUGCAGGCUG |
| 108 | hsa-miR-5006-3p | UUUCCCUUUCCAUCCUGGCAG |
| 109 | hsa-miR-4659a-3p | UUUCUUCUUAGACAUGGCAACG |
| 110 | brain-mir-279 | AUCCCACCGCUGCCACAC |
| 111 | brain-mir-111 | CACUGCUAAAUUUGGCUGGCUU |
| 112 | brain-mir-88 | UCUUCACCUGCCUCUGCCUGCA |
| 113 | brain-mir-251 | UGGCCCAAGACCUCAGACC |
| 114 | hsa-miR-4435 | AUGGCCAGAGCUCACACAGAGG |
| 115 | hsa-miR-5690 | UCAGCUACUACCUCUAUUAGG |
| 116 | brain-mir-166 | CUGGCUGCUUCCCUUGGUCU |
| 117 | brain-mir-193 | AUCCCUUUAUCUGUCCUCUAGG |
| 118 | hsa-miR-625-5p | AGGGGGAAAGUUCUAUAGUCC |
| 119 | hsa-miR-10b-5p | UACCCUGUAGAACCGAAUUUGUG |
| 120 | brain-mir-299 | CAUGCCACUGCACUCCAGCCU |
| 121 | brain-mir-153 | CCUCUUCUCAGAACACUUCCUGG |
| 122 | hsa-miR-758 | UUUGUGACCUGGUCCACUAACC |
| 123 | hsa-miR-30a-3p | CUUUCAGUCGGAUGUUUGCAGC |
| 124 | brain-mir-220 | UCCGGAUCCGGCUCCGCGCCU |
| 125 | brain-mir-392 | CCCGCCUGUCUCUCUCUUGCA |
| 126 | brain-mir-102 | UAUGGAGGUCUCUGUCUGGCU |
| 127 | hsa-let-7b-3p | CUAUACAACCUACUGCCUUCCC |
| 128 | hsa-miR-340-3p | UCCGUCUCAGUUACUUUAUAGC |
| 129 | hsa-miR-484 | UCAGGCUCAGUCCCCUCCCGAU |
| 130 | hsa-miR-30e-3p | CUUUCAGUCGGAUGUUUACAGC |
| 131 | brain-mir-72S | GACCACACUCCAUCCUGGGC |
| 132 | hsa-miR-371b-5p | ACUCAAAAGAUGGCGGCACUUU |
| 133 | hsa-miR-5581-3p | UUCCAUGCCUCCUAGAAGUUCC |
| 134 | brain-mir-399 | CACUGCAACCUCUGCCUCC |
| 135 | brain-mir-403 | AAAGACUUCCUUCUCUCGCCU |
| 136 | brain-mir-73 | UCCGGAUGUGCUGACCCCUGCG |
| 137 | brain-mir-190 | CCUGACCCCAUGUCGCCUCUGU |
| 138 | brain-mir-188 | CCUGACCCCAUGUCGCCUCUGU |
| 139 | brain-mir-189 | CCUGACCCCAUGUCGCCUCUGU |
| 140 | brain-mir-192 | CCUGACCCCAUGUCGCCUCUGU |
| 141 | brain-mir-311 | CACUGCAACCUCUGCCUCCCGA |
| 142 | brain-mir-161 | CUUCGAAAGCGGCUUCGGCU |
| 143 | hsa-miR-3074-5p | GUUCCUGCUGAACUGAGCCAG |
| 144 | hsa-miR-30b-5p | UGUAAACAUCCUACACUCAGCU |
| 145 | hsa-miR-576-5p | AUUCUAAUUUCUCCACGUCUUU |
| 146 | brain-mir-23 | UUAGUGGCUCCCUCUGCCUGCA |
| 147 | hsa-miR-943 | CUGACUGUUGCCGUCCUCCAG |
| 148 | brain-mir-351 | UGUCUUGCUCUGUUGCCCAGGU |
| 149 | hsa-miR-4772-3p | CCUGCAACUUUGCCUGAUCAGA |
| 150 | brain-mir-319 | CUGCACUCCAGCCUGGGCGA |
| 151 | hsa-miR-937 | AUCCGCGCUCUGACUCUCUGCC |
| 152 | hsa-miR-181a-2-3p | ACCACUGACCGUUGACUGUACC |
| 153 | hsa-miR-4755-5p | UUUCCCUUCAGAGCCUGGCUUU |
| 154 | hsa-miR-3909 | UGUCCUCUAGGGCCUGCAGUCU |
| 155 | hsa-miR-1260b | AUCCCACCACUGCCACCAU |
| 156 | brain-mir-293 | UUGGUGAGGACCCCAAGCUCGG |
| 157 | brain-mir-160 | CACUGCAACCUCUGCCUCC |
| 158 | hsa-miR-2110 | UUGGGGAAACGGCCGCUGAGUG |
| 159 | hsa-miR-584-3p | UCAGUUCCAGGCCAACCAGGCU |
| 160 | brain-mir-129 | CAUGGUCCAUUUUGCUCUGCU |

Supplemental Table 2
Overview of miRNA markers, including sequence information

| | | |
|---|---|---|
| 161 | hsa-miR-1280 | UCCCACCGCUGCCACCC |
| 162 | hsa-miR-3180-5p | CUUCCAGACGCUCCGCCCCACGUCG |
| 163 | hsa-miR-668 | UGUCACUCGGCUCGGCCCACUAC |
| 164 | hsa-miR-4512 | CAGGGCCUCACUGUAUCGCCCA |
| 165 | hsa-miR-641 | AAAGACAUAGGAUAGAGUCACCUC |
| 166 | hsa-miR-1233 | UGAGCCCUGUCCUCCCGCAG |
| 167 | hsa-miR-378a-5p | CUCCUGACUCCAGGUCCUGUGU |
| 168 | hsa-miR-26a-5p | UUCAAGUAAUCCAGGAUAGGCU |
| 169 | brain-mir-258 | AUCCCACCCCUGCCCCCA |
| 170 | hsa-miR-1260a | AUCCCACCUCUGCCACCA |
| 171 | hsa-miR-29c-3p | UAGCACCAUUUGAAAUCGGUUA |
| 172 | hsa-miR-29a-3p | UAGCACCAUCUGAAAUCGGUUA |
| 173 | hsa-let-7e-5p | UGAGGUAGGAGGUUGUAUAGUU |
| 174 | hsa-let-7a-5p | UGAGGUAGUAGGUUGUAUAGUU |
| 175 | hsa-let-7f-5p | UGAGGUAGUAGAUUGUAUAGUU |
| 176 | hsa-miR-29b-3p | UAGCACCAUUUGAAAUCAGUGUU |
| 177 | hsa-miR-98 | UGAGGUAGUAAGUUGUAUUGUU |
| 178 | hsa-miR-425-5p | AAUGACACGAUCACUCCCGUUGA |
| 179 | hsa-miR-223-3p | UGUCAGUUUGUCAAAUACCCCA |
| 180 | hsa-miR-181a-2-3p | ACCACUGACCGUUGACUGUACC |
| 181 | hsa-miR-148b-3p | UCAGUGCAUCACAGAACUUUGU |
| 182 | brain-mir-145 | AAGCACGCCUUUGAACCUGA |
| 183 | hsa-miR-548h-5p | AAAAGUAAUCGCGGUUUUUGUC |
| 184 | hsa-miR-550a-5p | AGUGCCUGAGGGAGUAAGAGCCC |
| 185 | hsa-miR-374b-5p | AUAUAAUACAACCUGCUAAGUG |
| 186 | hsa-miR-339-3p | UGAGCGCCUCGACGACAGAGCCG |
| 187 | hsa-miR-3661 | UGACCUGGGACUCGGACAGCUG |
| 188 | brain-mir-190 | CCUGACCCCAUGUCGCCUCUGU |
| 189 | brain-mir-188 | CCUGACCCCAUGUCGCCUCUGU |
| 190 | brain-mir-189 | CCUGACCCCAUGUCGCCUCUGU |
| 191 | brain-mir-192 | CCUGACCCCAUGUCGCCUCUGU |
| 192 | hsa-miR-550a-3-5p | AGUGCCUGAGGGAGUAAGAG |
| 193 | hsa-miR-199a-3p | ACAGUAGUCUGCACAUUGGUUA |
| 194 | hsa-miR-199b-3p | ACAGUAGUCUGCACAUUGGUUA |
| 195 | hsa-miR-660-5p | UACCCAUUGCAUAUCGGAGUUG |
| 196 | hsa-miR-190a | UGAUAUGUUUGAUAUAUUAGGU |
| 197 | brain-mir-220 | UCCGGAUCCGGCUCCGCGCCU |
| 198 | hsa-miR-548g-5p | UGCAAAAGUAAUUGCAGUUUUUG |
| 199 | hsa-miR-548ar-5p | AAAAGUAAUUGCAGUUUUUGC |
| 200 | hsa-miR-548x-5p | UGCAAAAGUAAUUGCAGUUUUUG |
| 201 | hsa-miR-548aj-5p | UGCAAAAGUAAUUGCAGUUUUUG |
| 202 | brain-mir-394 | AAAAGUAAUCGUAGUUUUUG |
| 203 | brain-mir-149 | AAAAGUAAUCGCACUUUUUG |
| 204 | brain-mir-151 | AAAAGUAAUCGCACUUUUUG |
| 205 | hsa-let-7c | UGAGGUAGUAGGUUGUAUGGUU |
| 206 | brain-mir-333 | AAAAGUAAUCGCAGGUUUUG |
| 207 | brain-mir-170 | AAAAGUAAUGGCAGUUUUUG |
| 208 | hsa-miR-152 | UCAGUGCAUGACAGAACUUGG |
| 209 | hsa-miR-15a-5p | UAGCAGCACAUAAUGGUUUGUG |
| 210 | hsa-miR-197-5p | CGGGUAGAGAGGGCAGUGGGAGG |
| 211 | brain-mir-399 | CACUGCAACCUCUGCCUCC |
| 212 | hsa-miR-3158-3p | AAGGGCUUCCUCUCUGCAGGAC |
| 213 | brain-mir-150 | UGAGGUAGUAGGUGGUGUGC |
| 214 | hsa-miR-424-3p | CAAAACGUGAGGCGCUGCUAU |
| 215 | hsa-miR-148a-3p | UCAGUGCACUACAGAACUUUGU |
| 216 | hsa-miR-3200-3p | CACCUUGCGCUACUCAGGUCUG |
| 217 | hsa-miR-628-3p | UCUAGUAAGAGUGGCAGUCGA |
| 218 | hsa-let-7d-5p | AGAGGUAGUAGGUUGCAUAGUU |
| 219 | hsa-miR-4781-3p | AAUGUUGGAAUCCUCGCUAGAG |
| 220 | brain-mir-160 | CACUGCAACCUCUGCCUCC |
| 221 | hsa-miR-374a-5p | UUAUAAUACAACCUGAUAAGUG |
| 222 | hsa-miR-338-3p | UCCAGCAUCAGUGAUUUUGUUG |
| 223 | hsa-miR-340-5p | UUAUAAAGCAAUGAGACUGAUU |
| 224 | brain-mir-395 | CACUGCACUCCAGCCUGGGUGA |
| 225 | brain-mir-308 | CACUGCACUCCAGCCUGGGUGA |
| 226 | brain-mir-53 | CCCAGGACAGUUUCAGUGAUG |
| 227 | brain-mir-229 | AUCCCACCUCUGCUACCA |
| 228 | hsa-miR-151a-3p | CUAGACUGAAGCUCCUUGAGG |
| 229 | hsa-miR-1234 | UCGGCCUGACCACCCACCCCAC |

| | | -continued |
|---|---|---|
| | Supplemental Table 2 Overview of miRNA markers, including sequence information | |
| 230 | hsa-miR-874 | CUGCCCUGGCCCGAGGGACCGA |
| 231 | hsa-miR-548av-5p | AAAAGUACUUGCGGAUUU |
| 232 | hsa-miR-548k | AAAAGUACUUGCGGAUUUUGCU |

| | | -continued |
|---|---|---|
| | Supplemental Table 2 Overview of miRNA markers, including sequence information | |
| 233 | brain-mir-101 | AGACCUACUUAUCUACCAACA |
| 234 | hsa-miR-30d-5p | UGUAAACAUCCCCGACUGGAAG |
| 235 | hsa-miR-3200-5p | AAUCUGAGAAGGCGCACAAGGU |

What is claimed is:

1. A method of analyzing miRNA in a blood sample taken from a patient, said method comprising the step of:
   a) determining in said blood sample expression level of: miRNA having the nucleotide sequence of SEQ ID NO: 142 and miRNA having the nucleotide sequence of SEQ ID NO: 59.

2. The method according to claim 1, further comprising determining expression level miRNA having the nucleotide sequence of SEQ ID NO: 69.

3. The method according to claim 2, comprising determining expression level of: miRNA having the nucleotide sequence of SEQ ID NO: 69, miRNA having the nucleotide sequence of SEQ ID NO: 142, miRNA having the nucleotide sequence of SEQ ID NO: 2, miRNA having the nucleotide sequence of SEQ ID NO: 59, miRNA having the nucleotide sequence of SEQ ID NO: 58, and miRNA having the nucleotide sequence of SEQ ID NO: 65.

4. The method according to claim 1, wherein the determination of the expression level in step (a) is obtained by use of a method selected from the group consisting of a Sequencing-based method, an array based method and a polymerase chain reaction (PCR) based method.

5. The method according to claim 1, comprising determining expression levels of at least 2, 3, 4, 5, or 6 miRNAs.

6. The method according to claim 1, wherein the patient is a healthy subject.

7. The method according to claim 1, wherein the patient is suffering from or at risk of developing Parkinson's Disease (PD) or a neurological disease other than PD.

8. The method according to claim 7, wherein the other neurological disease is selected from the group consisting of Alzheimer's disease (AD), Cognitive Impairment (MCI), Multiple Sclerosis (MS), Mild Depression, Bipolar Disorder (BD), and Schizophrenia.

9. The method of claim 1, wherein the blood sample is a blood cell sample.

10. The method of claim 7, wherein the patient has early symptoms of Parkinson's Disease (PD) or a neurological disease other than PD.

11. The method according to claim 4, wherein the determination of the expression level in step (a) is obtained by next-generation sequencing (NGS) or quantitative reverse transcription PCR (qRT-PCR).

12. The method according to claim 1, further comprising determining expression level of miRNA having the nucleotide sequence of SEQ ID NO: 2.

13. The method according to claim 1, further comprising determining expression level of miRNA having the nucleotide sequence of SEQ ID NO: 58.

14. The method according to claim 1, further comprising determining expression level of miRNA having the nucleotide sequence of SEQ ID NO: 65.

* * * * *

SEQUENCE LISTING

<160> NUMBER OF SEQ ID NOS: 235

<210> SEQ ID NO 1
<211> LENGTH: 22
<212> TYPE: RNA
<213> ORGANISM: Homo sapiens

<400> SEQUENCE: 1
ggauaucauc auauacugua ag                                          22

<210> SEQ ID NO 2
<211> LENGTH: 22
<212> TYPE: RNA
<213> ORGANISM: Homo sapiens

<400> SEQUENCE: 2
ugagguagua gauuguauag uu                                          22

<210> SEQ ID NO 3
<211> LENGTH: 22
<212> TYPE: RNA
<213> ORGANISM: Homo sapiens

<400> SEQUENCE: 3
ugagguagga gguuguauag uu                                          22

<210> SEQ ID NO 4
<211> LENGTH: 22
<212> TYPE: RNA
<213> ORGANISM: Homo sapiens

<400> SEQUENCE: 4
ugagguagua gguuguauag uu                                          22

<210> SEQ ID NO 5
<211> LENGTH: 23
<212> TYPE: RNA
<213> ORGANISM: Homo sapiens

<400> SEQUENCE: 5
agcagcauug uacagggcua uca                                         23

<210> SEQ ID NO 6
<211> LENGTH: 22
<212> TYPE: RNA
<213> ORGANISM: Homo sapiens

<400> SEQUENCE: 6
ugagguagua guuuguacag uu                                          22

```
<210> SEQ ID NO 7
<211> LENGTH: 23
<212> TYPE: RNA
<213> ORGANISM: Homo sapiens

<400> SEQUENCE: 7
agcagcauug uacagggcua uga                                          23

<210> SEQ ID NO 8
<211> LENGTH: 22
<212> TYPE: RNA
<213> ORGANISM: Homo sapiens

<400> SEQUENCE: 8
ugagguagua aguuguauug uu                                           22

<210> SEQ ID NO 9
<211> LENGTH: 22
<212> TYPE: RNA
<213> ORGANISM: Homo sapiens

<400> SEQUENCE: 9
uagcaccauu ugaaaucggu ua                                           22

<210> SEQ ID NO 10
<211> LENGTH: 21
<212> TYPE: RNA
<213> ORGANISM: Homo sapiens

<400> SEQUENCE: 10
uacaguacug ugauaacuga a                                            21

<210> SEQ ID NO 11
<211> LENGTH: 22
<212> TYPE: RNA
<213> ORGANISM: Homo sapiens

<400> SEQUENCE: 11
aaaaguaauc gcgguuuuug uc                                           22

<210> SEQ ID NO 12
<211> LENGTH: 22
<212> TYPE: RNA
<213> ORGANISM: Homo sapiens

<400> SEQUENCE: 12
ccgcacugug gguacuugcu gc                                           22

<210> SEQ ID NO 13
<211> LENGTH: 22
<212> TYPE: RNA
<213> ORGANISM: Homo sapiens

<400> SEQUENCE: 13
uagcagcaca uaaugguuug ug                                           22

<210> SEQ ID NO 14
<211> LENGTH: 23
<212> TYPE: RNA
<213> ORGANISM: Homo sapiens

<400> SEQUENCE: 14
ugcaaaagua auugcaguuu uug                                          23
```

```
<210> SEQ ID NO 15
<211> LENGTH: 21
<212> TYPE: RNA
<213> ORGANISM: Homo sapiens

<400> SEQUENCE: 15
aaaaguaauu gcaguuuuug c                                              21

<210> SEQ ID NO 16
<211> LENGTH: 23
<212> TYPE: RNA
<213> ORGANISM: Homo sapiens

<400> SEQUENCE: 16
ugcaaaagua auugcaguuu uug                                            23

<210> SEQ ID NO 17
<211> LENGTH: 23
<212> TYPE: RNA
<213> ORGANISM: Homo sapiens

<400> SEQUENCE: 17
ugcaaaagua auugcaguuu uug                                            23

<210> SEQ ID NO 18
<211> LENGTH: 22
<212> TYPE: RNA
<213> ORGANISM: Homo sapiens

<400> SEQUENCE: 18
ugagguagua gguuguaugg uu                                             22

<210> SEQ ID NO 19
<211> LENGTH: 20
<212> TYPE: RNA
<213> ORGANISM: Homo sapiens

<400> SEQUENCE: 19
aaaaguaauc guaguuuuug                                                20

<210> SEQ ID NO 20
<211> LENGTH: 22
<212> TYPE: RNA
<213> ORGANISM: Homo sapiens

<400> SEQUENCE: 20
ugugagguug gcauuguugu cu                                             22

<210> SEQ ID NO 21
<211> LENGTH: 20
<212> TYPE: RNA
<213> ORGANISM: Homo sapiens

<400> SEQUENCE: 21
aaaaguaaug gcaguuuuug                                                20

<210> SEQ ID NO 22
<211> LENGTH: 22
<212> TYPE: RNA
<213> ORGANISM: Homo sapiens

<400> SEQUENCE: 22
acaguagucu gcacauuggu ua                                             22
```

```
<210> SEQ ID NO 23
<211> LENGTH: 20
<212> TYPE: RNA
<213> ORGANISM: Homo sapiens

<400> SEQUENCE: 23
aaaaguaauc gcacuuuuug                                               20

<210> SEQ ID NO 24
<211> LENGTH: 20
<212> TYPE: RNA
<213> ORGANISM: Homo sapiens

<400> SEQUENCE: 24
aaaaguaauc gcacuuuuug                                               20

<210> SEQ ID NO 25
<211> LENGTH: 24
<212> TYPE: RNA
<213> ORGANISM: Homo sapiens

<400> SEQUENCE: 25
ggcuggucug augguagugg guua                                          24

<210> SEQ ID NO 26
<211> LENGTH: 22
<212> TYPE: RNA
<213> ORGANISM: Homo sapiens

<400> SEQUENCE: 26
acaguagucu gcacauuggu ua                                            22

<210> SEQ ID NO 27
<211> LENGTH: 20
<212> TYPE: RNA
<213> ORGANISM: Homo sapiens

<400> SEQUENCE: 27
aaaaguaauc gcagguuuug                                               20

<210> SEQ ID NO 28
<211> LENGTH: 21
<212> TYPE: RNA
<213> ORGANISM: Homo sapiens

<400> SEQUENCE: 28
ucuaguaaga guggcagucg a                                             21

<210> SEQ ID NO 29
<211> LENGTH: 22
<212> TYPE: RNA
<213> ORGANISM: Homo sapiens

<400> SEQUENCE: 29
ugauauguuu gauauauuag gu                                            22

<210> SEQ ID NO 30
<211> LENGTH: 23
<212> TYPE: RNA
<213> ORGANISM: Homo sapiens

<400> SEQUENCE: 30
```
uagcaccauu ugaaaucagu guu                                          23

<210> SEQ ID NO 31
<211> LENGTH: 22
<212> TYPE: RNA
<213> ORGANISM: Homo sapiens

<400> SEQUENCE: 31
uacccauugc auaucggagu ug                                           22

<210> SEQ ID NO 32
<211> LENGTH: 21
<212> TYPE: RNA
<213> ORGANISM: Homo sapiens

<400> SEQUENCE: 32
ugagaugaag cacuguagcu c                                            21

<210> SEQ ID NO 33
<211> LENGTH: 18
<212> TYPE: RNA
<213> ORGANISM: Homo sapiens

<400> SEQUENCE: 33
aaaaguacuu gcggauuu                                                18

<210> SEQ ID NO 34
<211> LENGTH: 22
<212> TYPE: RNA
<213> ORGANISM: Homo sapiens

<400> SEQUENCE: 34
aaaaguacuu gcggauuuug cu                                           22

<210> SEQ ID NO 35
<211> LENGTH: 22
<212> TYPE: RNA
<213> ORGANISM: Homo sapiens

<400> SEQUENCE: 35
uagcaccauc ugaaaucggu ua                                           22

<210> SEQ ID NO 36
<211> LENGTH: 22
<212> TYPE: RNA
<213> ORGANISM: Homo sapiens

<400> SEQUENCE: 36
aaaaguaauu gcggauuuug cc                                           22

<210> SEQ ID NO 37
<211> LENGTH: 22
<212> TYPE: RNA
<213> ORGANISM: Homo sapiens

<400> SEQUENCE: 37
acugcaguga aggcacuugu ag                                           22

<210> SEQ ID NO 38
<211> LENGTH: 24
<212> TYPE: RNA
<213> ORGANISM: Homo sapiens

<400> SEQUENCE: 38

| | |
|---|---|
| ggcugguccg agugcagugg uguu | 24 |

<210> SEQ ID NO 39
<211> LENGTH: 22
<212> TYPE: RNA
<213> ORGANISM: Homo sapiens

<400> SEQUENCE: 39

| | |
|---|---|
| ucagugcacu acagaacuuu gu | 22 |

<210> SEQ ID NO 40
<211> LENGTH: 22
<212> TYPE: RNA
<213> ORGANISM: Homo sapiens

<400> SEQUENCE: 40

| | |
|---|---|
| ucguaccgug aguaauaaug cg | 22 |

<210> SEQ ID NO 41
<211> LENGTH: 20
<212> TYPE: RNA
<213> ORGANISM: Homo sapiens

<400> SEQUENCE: 41

| | |
|---|---|
| ugagguagua gguggugugc | 20 |

<210> SEQ ID NO 42
<211> LENGTH: 22
<212> TYPE: RNA
<213> ORGANISM: Homo sapiens

<400> SEQUENCE: 42

| | |
|---|---|
| ugagguagua guuugugcug uu | 22 |

<210> SEQ ID NO 43
<211> LENGTH: 20
<212> TYPE: RNA
<213> ORGANISM: Homo sapiens

<400> SEQUENCE: 43

| | |
|---|---|
| gugcauugcu guugcauugc | 20 |

<210> SEQ ID NO 44
<211> LENGTH: 22
<212> TYPE: RNA
<213> ORGANISM: Homo sapiens

<400> SEQUENCE: 44

| | |
|---|---|
| caccuugcgc uacucagguc ug | 22 |

<210> SEQ ID NO 45
<211> LENGTH: 22
<212> TYPE: RNA
<213> ORGANISM: Homo sapiens

<400> SEQUENCE: 45

| | |
|---|---|
| aaaaguaauu gcgguuuuug cc | 22 |

<210> SEQ ID NO 46
<211> LENGTH: 21
<212> TYPE: RNA
<213> ORGANISM: Homo sapiens

```
<400> SEQUENCE: 46
ucagugcaug acagaacuug g                                              21

<210> SEQ ID NO 47
<211> LENGTH: 22
<212> TYPE: RNA
<213> ORGANISM: Homo sapiens

<400> SEQUENCE: 47
aaaaguaauu gcgguuuuug cc                                             22

<210> SEQ ID NO 48
<211> LENGTH: 21
<212> TYPE: RNA
<213> ORGANISM: Homo sapiens

<400> SEQUENCE: 48
aaaaguaauu gcgguuuuug c                                              21

<210> SEQ ID NO 49
<211> LENGTH: 22
<212> TYPE: RNA
<213> ORGANISM: Homo sapiens

<400> SEQUENCE: 49
aaaaguaauu gcgguuuuug cc                                             22

<210> SEQ ID NO 50
<211> LENGTH: 19
<212> TYPE: RNA
<213> ORGANISM: Homo sapiens

<400> SEQUENCE: 50
ggcggcggag gcggcggug                                                 19

<210> SEQ ID NO 51
<211> LENGTH: 21
<212> TYPE: RNA
<213> ORGANISM: Homo sapiens

<400> SEQUENCE: 51
augaccuaug aauugacaga c                                              21

<210> SEQ ID NO 52
<211> LENGTH: 22
<212> TYPE: RNA
<213> ORGANISM: Homo sapiens

<400> SEQUENCE: 52
uuauaaagca augagacuga uu                                             22

<210> SEQ ID NO 53
<211> LENGTH: 24
<212> TYPE: RNA
<213> ORGANISM: Homo sapiens

<400> SEQUENCE: 53
uugcagcugc cugggaguga cuuc                                           24

<210> SEQ ID NO 54
<211> LENGTH: 21
<212> TYPE: RNA
<213> ORGANISM: Homo sapiens
```

```
<400> SEQUENCE: 54
aagcacugcc uuugaaccug a                                              21

<210> SEQ ID NO 55
<211> LENGTH: 22
<212> TYPE: RNA
<213> ORGANISM: Homo sapiens

<400> SEQUENCE: 55
agacccuggu cugcacucua uc                                             22

<210> SEQ ID NO 56
<211> LENGTH: 22
<212> TYPE: RNA
<213> ORGANISM: Homo sapiens

<400> SEQUENCE: 56
uguaaacauc cccgacugga ag                                             22

<210> SEQ ID NO 57
<211> LENGTH: 22
<212> TYPE: RNA
<213> ORGANISM: Homo sapiens

<400> SEQUENCE: 57
aauguuggaa uccucgcuag ag                                             22

<210> SEQ ID NO 58
<211> LENGTH: 21
<212> TYPE: RNA
<213> ORGANISM: Homo sapiens

<400> SEQUENCE: 58
cuagacugaa gcuccuugag g                                              21

<210> SEQ ID NO 59
<211> LENGTH: 21
<212> TYPE: RNA
<213> ORGANISM: Homo sapiens

<400> SEQUENCE: 59
agcucugucu gugucucuag g                                              21

<210> SEQ ID NO 60
<211> LENGTH: 22
<212> TYPE: RNA
<213> ORGANISM: Homo sapiens

<400> SEQUENCE: 60
cacuagauug ugagcuccug ga                                             22

<210> SEQ ID NO 61
<211> LENGTH: 22
<212> TYPE: RNA
<213> ORGANISM: Homo sapiens

<400> SEQUENCE: 61
ccuguucucc auuacuuggc uc                                             22

<210> SEQ ID NO 62
<211> LENGTH: 21
<212> TYPE: RNA
```

```
<213> ORGANISM: Homo sapiens

<400> SEQUENCE: 62
cuccguuugc cuguuucgcu g                                              21

<210> SEQ ID NO 63
<211> LENGTH: 21
<212> TYPE: RNA
<213> ORGANISM: Homo sapiens

<400> SEQUENCE: 63
ucacagugaa ccggucucuu u                                              21

<210> SEQ ID NO 64
<211> LENGTH: 23
<212> TYPE: RNA
<213> ORGANISM: Homo sapiens

<400> SEQUENCE: 64
agugccugag ggaguaagag ccc                                            23

<210> SEQ ID NO 65
<211> LENGTH: 22
<212> TYPE: RNA
<213> ORGANISM: Homo sapiens

<400> SEQUENCE: 65
uuuugugucu cccauccccc ag                                             22

<210> SEQ ID NO 66
<211> LENGTH: 22
<212> TYPE: RNA
<213> ORGANISM: Homo sapiens

<400> SEQUENCE: 66
aaguucuguu auacacucag gc                                             22

<210> SEQ ID NO 67
<211> LENGTH: 22
<212> TYPE: RNA
<213> ORGANISM: Homo sapiens

<400> SEQUENCE: 67
cacugcacuc cagccugggu ga                                             22

<210> SEQ ID NO 68
<211> LENGTH: 22
<212> TYPE: RNA
<213> ORGANISM: Homo sapiens

<400> SEQUENCE: 68
cacugcacuc cagccugggu ga                                             22

<210> SEQ ID NO 69
<211> LENGTH: 21
<212> TYPE: RNA
<213> ORGANISM: Homo sapiens

<400> SEQUENCE: 69
gaucucacuu uguugcccag g                                              21

<210> SEQ ID NO 70
<211> LENGTH: 22
```

```
<212> TYPE: RNA
<213> ORGANISM: Homo sapiens

<400> SEQUENCE: 70
uucugccucu guccaggucc uu                                            22

<210> SEQ ID NO 71
<211> LENGTH: 22
<212> TYPE: RNA
<213> ORGANISM: Homo sapiens

<400> SEQUENCE: 71
uccccuucug caggccugcu gg                                            22

<210> SEQ ID NO 72
<211> LENGTH: 22
<212> TYPE: RNA
<213> ORGANISM: Homo sapiens

<400> SEQUENCE: 72
cugcccuagu cuagcugaag cu                                            22

<210> SEQ ID NO 73
<211> LENGTH: 22
<212> TYPE: RNA
<213> ORGANISM: Homo sapiens

<400> SEQUENCE: 73
cucggccuuu gcucgcagca cu                                            22

<210> SEQ ID NO 74
<211> LENGTH: 20
<212> TYPE: RNA
<213> ORGANISM: Homo sapiens

<400> SEQUENCE: 74
agugccugag ggaguaagag                                               20

<210> SEQ ID NO 75
<211> LENGTH: 22
<212> TYPE: RNA
<213> ORGANISM: Homo sapiens

<400> SEQUENCE: 75
uuaucagaau cuccaggggu ac                                            22

<210> SEQ ID NO 76
<211> LENGTH: 20
<212> TYPE: RNA
<213> ORGANISM: Homo sapiens

<400> SEQUENCE: 76
cagggucucg uucuguugcc                                               20

<210> SEQ ID NO 77
<211> LENGTH: 22
<212> TYPE: RNA
<213> ORGANISM: Homo sapiens

<400> SEQUENCE: 77
ugagaaccac gucugcucug ag                                            22

<210> SEQ ID NO 78
```

```
<211> LENGTH: 23
<212> TYPE: RNA
<213> ORGANISM: Homo sapiens

<400> SEQUENCE: 78
aaugacacga ucacucccgu uga                                              23

<210> SEQ ID NO 79
<211> LENGTH: 22
<212> TYPE: RNA
<213> ORGANISM: Homo sapiens

<400> SEQUENCE: 79
uguaaacauc cucgacugga ag                                               22

<210> SEQ ID NO 80
<211> LENGTH: 20
<212> TYPE: RNA
<213> ORGANISM: Homo sapiens

<400> SEQUENCE: 80
cacugcacuc cagccuggcu                                                  20

<210> SEQ ID NO 81
<211> LENGTH: 20
<212> TYPE: RNA
<213> ORGANISM: Homo sapiens

<400> SEQUENCE: 81
cacugcacuc cagccuggcu                                                  20

<210> SEQ ID NO 82
<211> LENGTH: 22
<212> TYPE: RNA
<213> ORGANISM: Homo sapiens

<400> SEQUENCE: 82
ucucugggcc ugugucuuag gc                                               22

<210> SEQ ID NO 83
<211> LENGTH: 22
<212> TYPE: RNA
<213> ORGANISM: Homo sapiens

<400> SEQUENCE: 83
caaagaauuc uccuuuuggg cu                                               22

<210> SEQ ID NO 84
<211> LENGTH: 23
<212> TYPE: RNA
<213> ORGANISM: Homo sapiens

<400> SEQUENCE: 84
acugcaaccu ccaccuccug ggu                                              23

<210> SEQ ID NO 85
<211> LENGTH: 22
<212> TYPE: RNA
<213> ORGANISM: Homo sapiens

<400> SEQUENCE: 85
cuauacgacc ugcugccuuu cu                                               22
```

```
<210> SEQ ID NO 86
<211> LENGTH: 22
<212> TYPE: RNA
<213> ORGANISM: Homo sapiens

<400> SEQUENCE: 86
cuggcccucu cugcccuucc gu                                              22

<210> SEQ ID NO 87
<211> LENGTH: 23
<212> TYPE: RNA
<213> ORGANISM: Homo sapiens

<400> SEQUENCE: 87
uguaaacauc cuacacucuc agc                                             23

<210> SEQ ID NO 88
<211> LENGTH: 21
<212> TYPE: RNA
<213> ORGANISM: Homo sapiens

<400> SEQUENCE: 88
uuccuggcuc ucuguugcac a                                               21

<210> SEQ ID NO 89
<211> LENGTH: 22
<212> TYPE: RNA
<213> ORGANISM: Homo sapiens

<400> SEQUENCE: 89
aauugcacgg uauccaucug ua                                              22

<210> SEQ ID NO 90
<211> LENGTH: 23
<212> TYPE: RNA
<213> ORGANISM: Homo sapiens

<400> SEQUENCE: 90
ugagcgccuc gacgacagag ccg                                             23

<210> SEQ ID NO 91
<211> LENGTH: 22
<212> TYPE: RNA
<213> ORGANISM: Homo sapiens

<400> SEQUENCE: 91
cacugcaacc ucugccuccg gu                                              22

<210> SEQ ID NO 92
<211> LENGTH: 22
<212> TYPE: RNA
<213> ORGANISM: Homo sapiens

<400> SEQUENCE: 92
ucuucucugu uuuggccaug ug                                              22

<210> SEQ ID NO 93
<211> LENGTH: 22
<212> TYPE: RNA
<213> ORGANISM: Homo sapiens

<400> SEQUENCE: 93
gcugacuccu aguccagggc uc                                              22
```

```
<210> SEQ ID NO 94
<211> LENGTH: 24
<212> TYPE: RNA
<213> ORGANISM: Homo sapiens

<400> SEQUENCE: 94
acgcccacug cuucacuuga cuag                                              24

<210> SEQ ID NO 95
<211> LENGTH: 23
<212> TYPE: RNA
<213> ORGANISM: Homo sapiens

<400> SEQUENCE: 95
ucuguauucu ccuuugccug cag                                               23

<210> SEQ ID NO 96
<211> LENGTH: 24
<212> TYPE: RNA
<213> ORGANISM: Homo sapiens

<400> SEQUENCE: 96
acucccacug cuucacuuga uuag                                              24

<210> SEQ ID NO 97
<211> LENGTH: 24
<212> TYPE: RNA
<213> ORGANISM: Homo sapiens

<400> SEQUENCE: 97
acucccacug cuugacuuga cuag                                              24

<210> SEQ ID NO 98
<211> LENGTH: 22
<212> TYPE: RNA
<213> ORGANISM: Homo sapiens

<400> SEQUENCE: 98
uugcucugcu cucccuugua cu                                                22

<210> SEQ ID NO 99
<211> LENGTH: 21
<212> TYPE: RNA
<213> ORGANISM: Homo sapiens

<400> SEQUENCE: 99
cacugcacuc cagccugggu a                                                 21

<210> SEQ ID NO 100
<211> LENGTH: 22
<212> TYPE: RNA
<213> ORGANISM: Homo sapiens

<400> SEQUENCE: 100
ucaaguguca ucugucccua gg                                                22

<210> SEQ ID NO 101
<211> LENGTH: 23
<212> TYPE: RNA
<213> ORGANISM: Homo sapiens

<400> SEQUENCE: 101
uacccuguag auccgaauuu gug                                               23
```

<210> SEQ ID NO 102
<211> LENGTH: 23
<212> TYPE: RNA
<213> ORGANISM: Homo sapiens

<400> SEQUENCE: 102 ccuccuguu accuguccuc uag                                    23

<210> SEQ ID NO 103
<211> LENGTH: 21
<212> TYPE: RNA
<213> ORGANISM: Homo sapiens

<400> SEQUENCE: 103
cugcacucca gccugggcga c                                     21

<210> SEQ ID NO 104
<211> LENGTH: 21
<212> TYPE: RNA
<213> ORGANISM: Homo sapiens

<400> SEQUENCE: 104
cccaggacag uuucagugau g                                     21

<210> SEQ ID NO 105
<211> LENGTH: 22
<212> TYPE: RNA
<213> ORGANISM: Homo sapiens

<400> SEQUENCE: 105
uucagccagg cuagugcagu cu                                    22

<210> SEQ ID NO 106
<211> LENGTH: 22
<212> TYPE: RNA
<213> ORGANISM: Homo sapiens

<400> SEQUENCE: 106
ccccgcgcag guucgaaucc ug                                    22

<210> SEQ ID NO 107
<211> LENGTH: 20
<212> TYPE: RNA
<213> ORGANISM: Homo sapiens

<400> SEQUENCE: 107
caccccacca gugcaggcug                                       20

<210> SEQ ID NO 108
<211> LENGTH: 21
<212> TYPE: RNA
<213> ORGANISM: Homo sapiens

<400> SEQUENCE: 108
uuucccuuuc cauccuggca g                                     21

<210> SEQ ID NO 109
<211> LENGTH: 22
<212> TYPE: RNA
<213> ORGANISM: Homo sapiens

<400> SEQUENCE: 109 uucuucuua gacauggcaa cg                                              22

<210> SEQ ID NO 110
<211> LENGTH: 18
<212> TYPE: RNA
<213> ORGANISM: Homo sapiens

<400> SEQUENCE: 110
aucccaccgc ugccacac                                                  18

<210> SEQ ID NO 111
<211> LENGTH: 22
<212> TYPE: RNA
<213> ORGANISM: Homo sapiens

<400> SEQUENCE: 111
cacugcuaaa uuuggcuggc uu                                             22

<210> SEQ ID NO 112
<211> LENGTH: 22
<212> TYPE: RNA
<213> ORGANISM: Homo sapiens

<400> SEQUENCE: 112
ucuucaccug ccucugccug ca                                             22

<210> SEQ ID NO 113
<211> LENGTH: 19
<212> TYPE: RNA
<213> ORGANISM: Homo sapiens

<400> SEQUENCE: 113
uggcccaaga ccucagacc                                                 19

<210> SEQ ID NO 114
<211> LENGTH: 22
<212> TYPE: RNA
<213> ORGANISM: Homo sapiens

<400> SEQUENCE: 114
auggccagag cucacacaga gg                                             22

<210> SEQ ID NO 115
<211> LENGTH: 21
<212> TYPE: RNA
<213> ORGANISM: Homo sapiens

<400> SEQUENCE: 115
ucagcuacua ccucuauuag g                                              21

<210> SEQ ID NO 116
<211> LENGTH: 20
<212> TYPE: RNA
<213> ORGANISM: Homo sapiens

<400> SEQUENCE: 116
cuggcugcuu cccuuggucu                                                20

<210> SEQ ID NO 117
<211> LENGTH: 22
<212> TYPE: RNA
<213> ORGANISM: Homo sapiens

<400> SEQUENCE: 117
aucccuuuau cuguccucua gg                                         22

<210> SEQ ID NO 118
<211> LENGTH: 21
<212> TYPE: RNA
<213> ORGANISM: Homo sapiens

<400> SEQUENCE: 118 aggggggaaag uucuauaguc c                                         21

<210> SEQ ID NO 119
<211> LENGTH: 23
<212> TYPE: RNA
<213> ORGANISM: Homo sapiens

<400> SEQUENCE: 119
uacccuguag aaccgaauuu gug                                        23

<210> SEQ ID NO 120
<211> LENGTH: 21
<212> TYPE: RNA
<213> ORGANISM: Homo sapiens

<400> SEQUENCE: 120
caugccacug cacuccagcc u                                          21

<210> SEQ ID NO 121
<211> LENGTH: 23
<212> TYPE: RNA
<213> ORGANISM: Homo sapiens

<400> SEQUENCE: 121
ccucuucuca gaacacuucc ugg                                        23

<210> SEQ ID NO 122
<211> LENGTH: 22
<212> TYPE: RNA
<213> ORGANISM: Homo sapiens

<400> SEQUENCE: 122
uuugugaccu gguccacuaa cc                                         22

<210> SEQ ID NO 123
<211> LENGTH: 22
<212> TYPE: RNA
<213> ORGANISM: Homo sapiens

<400> SEQUENCE: 123
cuuucagucg gauguuugca gc                                         22

<210> SEQ ID NO 124
<211> LENGTH: 21
<212> TYPE: RNA
<213> ORGANISM: Homo sapiens

<400> SEQUENCE: 124
uccggauccg gcuccgcgcc u                                          21

<210> SEQ ID NO 125
<211> LENGTH: 21
<212> TYPE: RNA
<213> ORGANISM: Homo sapiens

<400> SEQUENCE: 125
cccgccuguc ucucucuugc a                                              21

<210> SEQ ID NO 126
<211> LENGTH: 21
<212> TYPE: RNA
<213> ORGANISM: Homo sapiens

<400> SEQUENCE: 126
uauggagguc ucugucuggc u                                              21

<210> SEQ ID NO 127
<211> LENGTH: 22
<212> TYPE: RNA
<213> ORGANISM: Homo sapiens

<400> SEQUENCE: 127
cuauacaacc uacugccuuc cc                                             22

<210> SEQ ID NO 128
<211> LENGTH: 22
<212> TYPE: RNA
<213> ORGANISM: Homo sapiens

<400> SEQUENCE: 128
uccgucucag uuacuuuaua gc                                             22

<210> SEQ ID NO 129
<211> LENGTH: 22
<212> TYPE: RNA
<213> ORGANISM: Homo sapiens

<400> SEQUENCE: 129
ucaggcucag uccccucccg au                                             22

<210> SEQ ID NO 130
<211> LENGTH: 22
<212> TYPE: RNA
<213> ORGANISM: Homo sapiens

<400> SEQUENCE: 130
cuuucagucg gauguuuaca gc                                             22

<210> SEQ ID NO 131
<211> LENGTH: 20
<212> TYPE: RNA
<213> ORGANISM: Homo sapiens

<400> SEQUENCE: 131
gaccacacuc cauccugggc                                                20

<210> SEQ ID NO 132
<211> LENGTH: 22
<212> TYPE: RNA
<213> ORGANISM: Homo sapiens

<400> SEQUENCE: 132
acucaaaaga uggcggcacu uu                                             22

<210> SEQ ID NO 133
<211> LENGTH: 22
<212> TYPE: RNA
<213> ORGANISM: Homo sapiens

```
<400> SEQUENCE: 133
uuccaugccu ccagaaguu cc                                              22

<210> SEQ ID NO 134
<211> LENGTH: 19
<212> TYPE: RNA
<213> ORGANISM: Homo sapiens

<400> SEQUENCE: 134
cacugcaacc ucugccucc                                                 19

<210> SEQ ID NO 135
<211> LENGTH: 21
<212> TYPE: RNA
<213> ORGANISM: Homo sapiens

<400> SEQUENCE: 135
aaagacuucc uucucucgcc u                                              21

<210> SEQ ID NO 136
<211> LENGTH: 22
<212> TYPE: RNA
<213> ORGANISM: Homo sapiens

<400> SEQUENCE: 136
uccggaugug cugaccccug cg                                             22

<210> SEQ ID NO 137
<211> LENGTH: 23
<212> TYPE: RNA
<213> ORGANISM: Homo sapiens

<400> SEQUENCE: 137
ccugaccccc augucgccuc ugu                                            23

<210> SEQ ID NO 138
<211> LENGTH: 23
<212> TYPE: RNA
<213> ORGANISM: Homo sapiens

<400> SEQUENCE: 138
ccugaccccc augucgccuc ugu                                            23

<210> SEQ ID NO 139
<211> LENGTH: 23
<212> TYPE: RNA
<213> ORGANISM: Homo sapiens

<400> SEQUENCE: 139
ccugaccccc augucgccuc ugu                                            23

<210> SEQ ID NO 140
<211> LENGTH: 23
<212> TYPE: RNA
<213> ORGANISM: Homo sapiens

<400> SEQUENCE: 140
ccugaccccc augucgccuc ugu                                            23

<210> SEQ ID NO 141
<211> LENGTH: 22
<212> TYPE: RNA
```

<213> ORGANISM: Homo sapiens

<400> SEQUENCE: 141
cacugcaacc ucugccuccc ga                                              22

<210> SEQ ID NO 142
<211> LENGTH: 20
<212> TYPE: RNA
<213> ORGANISM: Homo sapiens

<400> SEQUENCE: 142
cuucgaaagc ggcuucggcu                                                 20

<210> SEQ ID NO 143
<211> LENGTH: 21
<212> TYPE: RNA
<213> ORGANISM: Homo sapiens

<400> SEQUENCE: 143 guccugcug aacugagcca g                                                21

<210> SEQ ID NO 144
<211> LENGTH: 22
<212> TYPE: RNA
<213> ORGANISM: Homo sapiens

<400> SEQUENCE: 144
uguaaacauc cuacacucag cu                                              22

<210> SEQ ID NO 145
<211> LENGTH: 22
<212> TYPE: RNA
<213> ORGANISM: Homo sapiens

<400> SEQUENCE: 145
auucuaauuu cuccacgucu uu                                              22

<210> SEQ ID NO 146
<211> LENGTH: 22
<212> TYPE: RNA
<213> ORGANISM: Homo sapiens

<400> SEQUENCE: 146
uuaguggcuc ccucugccug ca                                              22

<210> SEQ ID NO 147
<211> LENGTH: 21
<212> TYPE: RNA
<213> ORGANISM: Homo sapiens

<400> SEQUENCE: 147
cugacuguug ccguccucca g                                               21

<210> SEQ ID NO 148
<211> LENGTH: 22
<212> TYPE: RNA
<213> ORGANISM: Homo sapiens

<400> SEQUENCE: 148
ugucuugcuc uguugcccag gu                                              22

<210> SEQ ID NO 149
<211> LENGTH: 22

```
<212> TYPE: RNA
<213> ORGANISM: Homo sapiens

<400> SEQUENCE: 149
ccugcaacuu ugccugauca ga                                              22

<210> SEQ ID NO 150
<211> LENGTH: 20
<212> TYPE: RNA
<213> ORGANISM: Homo sapiens

<400> SEQUENCE: 150
cugcacucca gccugggcga                                                 20

<210> SEQ ID NO 151
<211> LENGTH: 22
<212> TYPE: RNA
<213> ORGANISM: Homo sapiens

<400> SEQUENCE: 151
auccgcgcuc ugacucucug cc                                              22

<210> SEQ ID NO 152
<211> LENGTH: 22
<212> TYPE: RNA
<213> ORGANISM: Homo sapiens

<400> SEQUENCE: 152
accacugacc guugacugua cc                                              22

<210> SEQ ID NO 153
<211> LENGTH: 22
<212> TYPE: RNA
<213> ORGANISM: Homo sapiens

<400> SEQUENCE: 153
uuucccuuca gagccuggcu uu                                              22

<210> SEQ ID NO 154
<211> LENGTH: 22
<212> TYPE: RNA
<213> ORGANISM: Homo sapiens

<400> SEQUENCE: 154
uguccucuag ggccugcagu cu                                              22

<210> SEQ ID NO 155
<211> LENGTH: 19
<212> TYPE: RNA
<213> ORGANISM: Homo sapiens

<400> SEQUENCE: 155
aucccaccac ugccaccau                                                  19

<210> SEQ ID NO 156
<211> LENGTH: 22
<212> TYPE: RNA
<213> ORGANISM: Homo sapiens

<400> SEQUENCE: 156
uuggugagga ccccaagcuc gg                                              22

<210> SEQ ID NO 157
```

```
<211> LENGTH: 19
<212> TYPE: RNA
<213> ORGANISM: Homo sapiens

<400> SEQUENCE: 157
cacugcaacc ucugccucc                                                   19

<210> SEQ ID NO 158
<211> LENGTH: 22
<212> TYPE: RNA
<213> ORGANISM: Homo sapiens

<400> SEQUENCE: 158 uugggggaaac ggccgcugag ug                                              22

<210> SEQ ID NO 159
<211> LENGTH: 22
<212> TYPE: RNA
<213> ORGANISM: Homo sapiens

<400> SEQUENCE: 159
ucaguuccag gccaaccagg cu                                               22

<210> SEQ ID NO 160
<211> LENGTH: 21
<212> TYPE: RNA
<213> ORGANISM: Homo sapiens

<400> SEQUENCE: 160
caugguccau uuugcucugc u                                                21

<210> SEQ ID NO 161
<211> LENGTH: 17
<212> TYPE: RNA
<213> ORGANISM: Homo sapiens

<400> SEQUENCE: 161
ucccaccgcu gccaccc                                                     17

<210> SEQ ID NO 162
<211> LENGTH: 25
<212> TYPE: RNA
<213> ORGANISM: Homo sapiens

<400> SEQUENCE: 162
cuuccagacg cuccgcccca cgucg                                            25

<210> SEQ ID NO 163
<211> LENGTH: 23
<212> TYPE: RNA
<213> ORGANISM: Homo sapiens

<400> SEQUENCE: 163
ugucacucgg cucggcccac uac                                              23

<210> SEQ ID NO 164
<211> LENGTH: 22
<212> TYPE: RNA
<213> ORGANISM: Homo sapiens

<400> SEQUENCE: 164
cagggccuca cuguaucgcc ca                                               22
```

```
<210> SEQ ID NO 165
<211> LENGTH: 24
<212> TYPE: RNA
<213> ORGANISM: Homo sapiens

<400> SEQUENCE: 165
aaagacauag gauagaguca ccuc                                          24

<210> SEQ ID NO 166
<211> LENGTH: 20
<212> TYPE: RNA
<213> ORGANISM: Homo sapiens

<400> SEQUENCE: 166
ugagcccugu ccucccgcag                                               20

<210> SEQ ID NO 167
<211> LENGTH: 22
<212> TYPE: RNA
<213> ORGANISM: Homo sapiens

<400> SEQUENCE: 167
cuccugacuc cagguccugu gu                                            22

<210> SEQ ID NO 168
<211> LENGTH: 22
<212> TYPE: RNA
<213> ORGANISM: Homo sapiens

<400> SEQUENCE: 168
uucaaguaau ccaggauagg cu                                            22

<210> SEQ ID NO 169
<211> LENGTH: 18
<212> TYPE: RNA
<213> ORGANISM: Homo sapiens

<400> SEQUENCE: 169
aucccacccc ugcccca                                                  18

<210> SEQ ID NO 170
<211> LENGTH: 18
<212> TYPE: RNA
<213> ORGANISM: Homo sapiens

<400> SEQUENCE: 170
aucccaccuc ugccacca                                                 18

<210> SEQ ID NO 171
<211> LENGTH: 22
<212> TYPE: RNA
<213> ORGANISM: Homo sapiens

<400> SEQUENCE: 171
uagcaccauu ugaaucggu ua                                             22

<210> SEQ ID NO 172
<211> LENGTH: 22
<212> TYPE: RNA
<213> ORGANISM: Homo sapiens

<400> SEQUENCE: 172
uagcaccauc ugaaaucggu ua                                            22
```

<210> SEQ ID NO 173
<211> LENGTH: 22
<212> TYPE: RNA
<213> ORGANISM: Homo sapiens

<400> SEQUENCE: 173
ugagguagga gguuguauag uu                                              22

<210> SEQ ID NO 174
<211> LENGTH: 22
<212> TYPE: RNA
<213> ORGANISM: Homo sapiens

<400> SEQUENCE: 174
ugagguagua gguuguauag uu                                              22

<210> SEQ ID NO 175
<211> LENGTH: 22
<212> TYPE: RNA
<213> ORGANISM: Homo sapiens

<400> SEQUENCE: 175
ugagguagua gauuguauag uu                                              22

<210> SEQ ID NO 176
<211> LENGTH: 23
<212> TYPE: RNA
<213> ORGANISM: Homo sapiens

<400> SEQUENCE: 176
uagcaccauu ugaaaucagu guu                                             23

<210> SEQ ID NO 177
<211> LENGTH: 22
<212> TYPE: RNA
<213> ORGANISM: Homo sapiens

<400> SEQUENCE: 177
ugagguagua aguuguauug uu                                              22

<210> SEQ ID NO 178
<211> LENGTH: 23
<212> TYPE: RNA
<213> ORGANISM: Homo sapiens

<400> SEQUENCE: 178
aaugacacga ucacucccgu uga                                             23

<210> SEQ ID NO 179
<211> LENGTH: 22
<212> TYPE: RNA
<213> ORGANISM: Homo sapiens

<400> SEQUENCE: 179
ugucaguuug ucaaauaccc ca                                              22

<210> SEQ ID NO 180
<211> LENGTH: 22
<212> TYPE: RNA
<213> ORGANISM: Homo sapiens

<400> SEQUENCE: 180
accacugacc guugacugua cc                                              22

```
<210> SEQ ID NO 181
<211> LENGTH: 22
<212> TYPE: RNA
<213> ORGANISM: Homo sapiens

<400> SEQUENCE: 181
ucagugcauc acagaacuuu gu                                              22

<210> SEQ ID NO 182
<211> LENGTH: 21
<212> TYPE: RNA
<213> ORGANISM: Homo sapiens

<400> SEQUENCE: 182
aagcacugcc uuugaaccug a                                               21

<210> SEQ ID NO 183
<211> LENGTH: 22
<212> TYPE: RNA
<213> ORGANISM: Homo sapiens

<400> SEQUENCE: 183
aaaaguaauc gcgguuuuug uc                                              22

<210> SEQ ID NO 184
<211> LENGTH: 23
<212> TYPE: RNA
<213> ORGANISM: Homo sapiens

<400> SEQUENCE: 184
agugccugag ggaguaagag ccc                                             23

<210> SEQ ID NO 185
<211> LENGTH: 22
<212> TYPE: RNA
<213> ORGANISM: Homo sapiens

<400> SEQUENCE: 185
auauaauaca accugcuaag ug                                              22

<210> SEQ ID NO 186
<211> LENGTH: 23
<212> TYPE: RNA
<213> ORGANISM: Homo sapiens

<400> SEQUENCE: 186
ugagcgccuc gacgacagag ccg                                             23

<210> SEQ ID NO 187
<211> LENGTH: 22
<212> TYPE: RNA
<213> ORGANISM: Homo sapiens

<400> SEQUENCE: 187
ugaccuggga cucggacagc ug                                              22

<210> SEQ ID NO 188
<211> LENGTH: 23
<212> TYPE: RNA
<213> ORGANISM: Homo sapiens

<400> SEQUENCE: 188
```
ccugaccccc augucgccuc ugu                                              23

<210> SEQ ID NO 189
<211> LENGTH: 23
<212> TYPE: RNA
<213> ORGANISM: Homo sapiens

<400> SEQUENCE: 189
ccugaccccc augucgccuc ugu                                              23

<210> SEQ ID NO 190
<211> LENGTH: 23
<212> TYPE: RNA
<213> ORGANISM: Homo sapiens

<400> SEQUENCE: 190
ccugaccccc augucgccuc ugu                                              23

<210> SEQ ID NO 191
<211> LENGTH: 23
<212> TYPE: RNA
<213> ORGANISM: Homo sapiens

<400> SEQUENCE: 191
ccugaccccc augucgccuc ugu                                              23

<210> SEQ ID NO 192
<211> LENGTH: 20
<212> TYPE: RNA
<213> ORGANISM: Homo sapiens

<400> SEQUENCE: 192
agugccugag ggaguaagag                                                  20

<210> SEQ ID NO 193
<211> LENGTH: 22
<212> TYPE: RNA
<213> ORGANISM: Homo sapiens

<400> SEQUENCE: 193
acaguagucu gcacauuggu ua                                               22

<210> SEQ ID NO 194
<211> LENGTH: 22
<212> TYPE: RNA
<213> ORGANISM: Homo sapiens

<400> SEQUENCE: 194
acaguagucu gcacauuggu ua                                               22

<210> SEQ ID NO 195
<211> LENGTH: 22
<212> TYPE: RNA
<213> ORGANISM: Homo sapiens

<400> SEQUENCE: 195
uacccauugc auaucggagu ug                                               22

<210> SEQ ID NO 196
<211> LENGTH: 22
<212> TYPE: RNA
<213> ORGANISM: Homo sapiens

<400> SEQUENCE: 196
ugauauguuu gauauauuag gu                                22

<210> SEQ ID NO 197
<211> LENGTH: 21
<212> TYPE: RNA
<213> ORGANISM: Homo sapiens

<400> SEQUENCE: 197
uccggauccg gcuccgcgcc u                                 21

<210> SEQ ID NO 198
<211> LENGTH: 23
<212> TYPE: RNA
<213> ORGANISM: Homo sapiens

<400> SEQUENCE: 198
ugcaaaagua auugcaguuu uug                               23

<210> SEQ ID NO 199
<211> LENGTH: 21
<212> TYPE: RNA
<213> ORGANISM: Homo sapiens

<400> SEQUENCE: 199
aaaaguaauu gcaguuuuug c                                 21

<210> SEQ ID NO 200
<211> LENGTH: 23
<212> TYPE: RNA
<213> ORGANISM: Homo sapiens

<400> SEQUENCE: 200
ugcaaaagua auugcaguuu uug                               23

<210> SEQ ID NO 201
<211> LENGTH: 23
<212> TYPE: RNA
<213> ORGANISM: Homo sapiens

<400> SEQUENCE: 201
ugcaaaagua auugcaguuu uug                               23

<210> SEQ ID NO 202
<211> LENGTH: 20
<212> TYPE: RNA
<213> ORGANISM: Homo sapiens

<400> SEQUENCE: 202
aaaaguaauc guaguuuuug                                   20

<210> SEQ ID NO 203
<211> LENGTH: 20
<212> TYPE: RNA
<213> ORGANISM: Homo sapiens

<400> SEQUENCE: 203
aaaaguaauc gcacuuuuug                                   20

<210> SEQ ID NO 204
<211> LENGTH: 20
<212> TYPE: RNA
<213> ORGANISM: Homo sapiens

```
<400> SEQUENCE: 204
aaaaguaauc gcacuuuug                                                   20

<210> SEQ ID NO 205
<211> LENGTH: 22
<212> TYPE: RNA
<213> ORGANISM: Homo sapiens

<400> SEQUENCE: 205
ugagguagua gguuguaugg uu                                               22

<210> SEQ ID NO 206
<211> LENGTH: 20
<212> TYPE: RNA
<213> ORGANISM: Homo sapiens

<400> SEQUENCE: 206
aaaaguaauc gcagguuuug                                                  20

<210> SEQ ID NO 207
<211> LENGTH: 20
<212> TYPE: RNA
<213> ORGANISM: Homo sapiens

<400> SEQUENCE: 207
aaaaguaaug gcaguuuuug                                                  20

<210> SEQ ID NO 208
<211> LENGTH: 21
<212> TYPE: RNA
<213> ORGANISM: Homo sapiens

<400> SEQUENCE: 208
ucagugcaug acagaacuug g                                                21

<210> SEQ ID NO 209
<211> LENGTH: 22
<212> TYPE: RNA
<213> ORGANISM: Homo sapiens

<400> SEQUENCE: 209
uagcagcaca uaaugguuug ug                                               22

<210> SEQ ID NO 210
<211> LENGTH: 23
<212> TYPE: RNA
<213> ORGANISM: Homo sapiens

<400> SEQUENCE: 210
cggguagaga gggcaguggg agg                                              23

<210> SEQ ID NO 211
<211> LENGTH: 19
<212> TYPE: RNA
<213> ORGANISM: Homo sapiens

<400> SEQUENCE: 211
cacugcaacc ucugccucc                                                   19

<210> SEQ ID NO 212
<211> LENGTH: 22
<212> TYPE: RNA
<213> ORGANISM: Homo sapiens
```

```
<400> SEQUENCE: 212
aagggcuucc ucucugcagg ac                                              22

<210> SEQ ID NO 213
<211> LENGTH: 20
<212> TYPE: RNA
<213> ORGANISM: Homo sapiens

<400> SEQUENCE: 213
ugagguagua gguggugugc                                                 20

<210> SEQ ID NO 214
<211> LENGTH: 21
<212> TYPE: RNA
<213> ORGANISM: Homo sapiens

<400> SEQUENCE: 214
caaaacguga ggcgcugcua u                                               21

<210> SEQ ID NO 215
<211> LENGTH: 22
<212> TYPE: RNA
<213> ORGANISM: Homo sapiens

<400> SEQUENCE: 215
ucagugcacu acagaacuuu gu                                              22

<210> SEQ ID NO 216
<211> LENGTH: 22
<212> TYPE: RNA
<213> ORGANISM: Homo sapiens

<400> SEQUENCE: 216
caccuugcgc uacucagguc ug                                              22

<210> SEQ ID NO 217
<211> LENGTH: 21
<212> TYPE: RNA
<213> ORGANISM: Homo sapiens

<400> SEQUENCE: 217
ucuaguaaga guggcagucg a                                               21

<210> SEQ ID NO 218
<211> LENGTH: 22
<212> TYPE: RNA
<213> ORGANISM: Homo sapiens

<400> SEQUENCE: 218
agagguagua gguugcauag uu                                              22

<210> SEQ ID NO 219
<211> LENGTH: 22
<212> TYPE: RNA
<213> ORGANISM: Homo sapiens

<400> SEQUENCE: 219
aauguuggaa uccucgcuag ag                                              22

<210> SEQ ID NO 220
<211> LENGTH: 19
<212> TYPE: RNA
```

```
<213> ORGANISM: Homo sapiens

<400> SEQUENCE: 220
cacugcaacc ucugccucc                                                  19

<210> SEQ ID NO 221
<211> LENGTH: 22
<212> TYPE: RNA
<213> ORGANISM: Homo sapiens

<400> SEQUENCE: 221
uuauaauaca accugauaag ug                                              22

<210> SEQ ID NO 222
<211> LENGTH: 22
<212> TYPE: RNA
<213> ORGANISM: Homo sapiens

<400> SEQUENCE: 222
uccagcauca gugauuuugu ug                                              22

<210> SEQ ID NO 223
<211> LENGTH: 22
<212> TYPE: RNA
<213> ORGANISM: Homo sapiens

<400> SEQUENCE: 223
uuauaaagca augagacuga uu                                              22

<210> SEQ ID NO 224
<211> LENGTH: 22
<212> TYPE: RNA
<213> ORGANISM: Homo sapiens

<400> SEQUENCE: 224
cacugcacuc cagccugggu ga                                              22

<210> SEQ ID NO 225
<211> LENGTH: 22
<212> TYPE: RNA
<213> ORGANISM: Homo sapiens

<400> SEQUENCE: 225
cacugcacuc cagccugggu ga                                              22

<210> SEQ ID NO 226
<211> LENGTH: 21
<212> TYPE: RNA
<213> ORGANISM: Homo sapiens

<400> SEQUENCE: 226
cccaggacag uuucagugau g                                               21

<210> SEQ ID NO 227
<211> LENGTH: 18
<212> TYPE: RNA
<213> ORGANISM: Homo sapiens

<400> SEQUENCE: 227
aucccaccuc ugcuacca                                                   18

<210> SEQ ID NO 228
<211> LENGTH: 21
```

```
<212> TYPE: RNA
<213> ORGANISM: Homo sapiens

<400> SEQUENCE: 228
cuagacugaa gcuccuugag g                                               21

<210> SEQ ID NO 229
<211> LENGTH: 22
<212> TYPE: RNA
<213> ORGANISM: Homo sapiens

<400> SEQUENCE: 229
ucggccugac cacccacccc ac                                              22

<210> SEQ ID NO 230
<211> LENGTH: 22
<212> TYPE: RNA
<213> ORGANISM: Homo sapiens

<400> SEQUENCE: 230
cugcccuggc ccgagggacc ga                                              22

<210> SEQ ID NO 231
<211> LENGTH: 18
<212> TYPE: RNA
<213> ORGANISM: Homo sapiens

<400> SEQUENCE: 231
aaaaguacuu gcggauuu                                                   18

<210> SEQ ID NO 232
<211> LENGTH: 22
<212> TYPE: RNA
<213> ORGANISM: Homo sapiens

<400> SEQUENCE: 232
aaaaguacuu gcggauuuug cu                                              22

<210> SEQ ID NO 233
<211> LENGTH: 21
<212> TYPE: RNA
<213> ORGANISM: Homo sapiens

<400> SEQUENCE: 233
agaccuacuu aucuaccaac a                                               21

<210> SEQ ID NO 234
<211> LENGTH: 22
<212> TYPE: RNA
<213> ORGANISM: Homo sapiens

<400> SEQUENCE: 234
uguaaacauc cccgacugga ag                                              22

<210> SEQ ID NO 235
<211> LENGTH: 22
<212> TYPE: RNA
<213> ORGANISM: Homo sapiens

<400> SEQUENCE: 235
aaucugagaa ggcgcacaag gu                                              22
```